US006093801A

United States Patent [19]

Scott et al.

[11] Patent Number: 6,093,801

[45] Date of Patent: Jul. 25, 2000

[54] RECOMBINANT ANALOGS OF BACTERICIDAL/PERMEABILITY INCREASING PROTEIN

[75] Inventors: Randal W. Scott, Cupertino; Marian N. Marra, San Mateo, both of Calif.

[73] Assignee: Incyte Pharmaceuticals, Inc., Palo Alto, Calif.

[21] Appl. No.: 09/025,543

[22] Filed: Feb. 18, 1998

Related U.S. Application Data

[63] Continuation of application No. 07/915,720, filed as application No. PCT/US91/05758, Aug. 13, 1991, which is a continuation-in-part of application No. 07/681,551, Apr. 5, 1991, Pat. No. 5,171,739, which is a continuation-in-part of application No. 07/567,016, Aug. 13, 1990, abandoned, which is a continuation-in-part of application No. 07/468,696, Jan. 22, 1990, Pat. No. 5,089,274, which is a continuation-in-part of application No. 07/310,842, Feb. 14, 1989, abandoned.

[51] Int. Cl.[7] ........................ C07K 14/00; C07K 14/435; A61K 38/03; A61K 38/17

[52] U.S. Cl. .......................... 530/350; 530/350; 530/829; 514/12; 514/21; 514/2; 435/69.1; 435/69.3; 435/7.1; 424/88; 424/92; 424/534

[58] Field of Search ............................... 424/534, 88, 92; 514/2, 21, 829, 12; 530/829, 350; 435/7.1, 69.1, 69.3

[56] References Cited

U.S. PATENT DOCUMENTS

| | | | |
|---|---|---|---|
| 5,234,912 | 8/1993 | Scott et al. | 514/21 |
| 5,308,834 | 5/1994 | Scott et al. | 514/12 |
| 5,334,584 | 8/1994 | Scott et al. | 514/12 |
| 5,770,694 | 6/1998 | Scott et al. | 530/350 |

FOREIGN PATENT DOCUMENTS

| | | |
|---|---|---|
| 0 272 489 | 6/1988 | European Pat. Off. . |
| WO 89/01486 | 2/1989 | WIPO . |
| WO 90/09183 | 8/1990 | WIPO . |

OTHER PUBLICATIONS

Marra et al., "Bactericidal/Permeability–Increasing Protein Has Endotoxin–Neutralizing Activity" *J. Immunol.* (1990) 144:662–666.

Elsbach et al., "Bactericidal/Permeability Increasing Protein (BPI) of Granulocytes: Structure and Function" *Bacteria–Host Cell Interaction* (1988) pp. 47–60.

Gray et al., "Cloning of the Gene of the Human Bactericidal/Permeability Increasing Protein and Identification of Structure–Function Relationships" *Clinical Research* (1988) 36(3):620A.

Gray et al., "Cloning of the cDNA of a Human Neutrophil Bactericidal Protein" *J. Biol. Chem.* (1989) 264(16):9505–9509.

Weiss et al., "Killing of Gram–Negative Bacteria by Polymorphonuclear Leukocytes" *The American Society of Clinical Investigation, Inc.* (1982) 69:959–970.

Weiss et al., "Oxygen–independent intracellular and Oxygen–dependent Extracellular Killing of *Escherichia coli* S15 by Human Polymorphonuclear Leukocytes" *The American Society of Clinical Investigation, Inc.* (1985) 76:206–212.

Leong et al., "Cloning of the cDNA of a Human Neutrophil Bactericidal Protein" *J. Cell Biochem. Suppl.* (1989) 13:66.

Weiss et al., "Sensitivity of K1–Encapsulated *Escherichia coli* to Killing by the Bactericidal/Permeability–Increasing Protein of Rabbit and Human Neutrophils" *Infection and Immunity* (1982) 38:1149–1153.

Muello et al., "The Role of Endotoxin in the Action of the Bactericidal/Permeability Increasing Neutrophil Protein on the Bacterial Envelope" *Clinical Research* (1983) 31(2):371A.

Weiss et al., "Role of Charge and Hydrophobic Interactions in the Action of the Bactericidal/Permeability–increasing Protein of Neutrophils on Gram–negative Bacteria" *J. Clin. Invest.* (1983) 71:540–549.

Shafer et al., "Cationic Antimicrobial Proteins Isolated from Human Neutrophil Granulocytes in the Presence of Diisopropyl Fluorophosphate" *Infection and Immunity* (1984) 45:29–35.

Hovde et al., "Characterization of a Protein from Normal Human Polymorphonuclear Leukocytes with Bactericidal Activity against *Pseudomonas aeruginosa" Infection and Immunity* (1986) 54(1):142–148.

Weiss et al., "Environmental Modulation of Lipopolysaccharide Chain Length Alters the Sensitivity of *Escherichia coli* to the Neutrophil Bactericidal/Permeability–Increasing Protein" *Infection and Immunity* (1986) 51(2):594–599.

Spitznagel et al., "A Monoclonal Antibody that Inhibits the Antimicrobial Action of a 57 KD Cationic Protein of Human Polymorphonuclear Leukocytes" *J. Immunol.* (1987) 139(4):1291–1296.

Farley et al., "Antimicrobial Binding of a Radiolabeled Cationic Neutrophil Granule Protein" *Infection and Immunity* (1987) 55(6):1536–1539.

Veld et al., "Effects of the Bactericidal/Permeability–Increasing Protein of Polymorphonuclear Leukocytes on Isolated Bacterial Cytoplasmic Membrane Vesicles" *Infection and Immunity* (1988) 56(5):1203–1208.

Farley et al., "Lipopolysaccharide Structure Determines Ionic and Hydrophobic Binding of a Cationic Antimicrobial Neutrophil Granule Protein" *Infection and Immunity* (1988) 56(6):1589–1592.

Mannion et al., "Preferential Binding of the Neutrophil Cytoplasmic Granule–Derived Bactericidal/Permeability Increasing Protein to Target Bacteria" *J. Immunol.* (1989) 142(8):2807–2812.

(List continued on next page.)

*Primary Examiner*—Nita Minnifield
*Assistant Examiner*—Padma Baskar
*Attorney, Agent, or Firm*—McAndrews, Held & Malloy, Ltd.

[57] ABSTRACT

The present invention provides a composition comprising a BPI Protein and an anionic compound which composition exhibits (1) no bacterial activity and (2) endotoxin neutralizing activity. Also, this invention provides methods for using BPI Proteins.

2 Claims, 26 Drawing Sheets

OTHER PUBLICATIONS

Weiss et al., "The Bactericidal/Permeability–Increasing Protein of Neutrophils Retains its Biological Activities After Cleavage by Neutrophil Proteases" *ASCI Metabolism* (1985) 33(2):567A.

Mannion et al., "Separation of Sublethal and Lethal Effects of the Bactericidal/Permeability Increasing Protein on *Escherichia coli" J. Clin. Invest*. (1990) 85:853–860.

Pereira et al., "The Ontogeny of a 57–Kd Cationic Antimicrobial Protein of Human Polymorphonuclear Leukocytes: Localization to a Novel Granule Population" *Blood* (1990) 76(4):825–834.

Schumann et al., "Structure and Function of Lipopolysaccharide Binding Protein" *Science* (1990) 249:1429–1431.

Larrick et al., "Complementary DNA sequence of rabbit CAP18—a unique lipopolysaccharide binding protein" *Biochem. Biophys. Res. Commun*. (1991) 179(1):170–175.

Cross et al., "Choice of Bacteria in Animal Models of Sepsis" *Infection and Immunity* (1993) 61(7):2741–2747.

Ooi et al., "A 25–kDa $NH_2$–terminal Fragment Carries All the Antibacterial Activities of the Human Neutrophil 60–kDa Bactericidal/Permeability–increasing Protein" *J. Biol. Chem*. (1987) 262(31):14891–14894.

Tobias et al., "A Family of Lipopolysaccharide Binding Proteins Involved in Responses to Gram–negative Sepsis" *J. Biol. Chem*. (1988) 263(27):13479–13481.

Ooi et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils" *J. Exp. Med*. (1991) 174:649–655.

Geisow, "Glycoprotein glycans—roles and controls" *Tibech* (1992) 10:333–335.

Bowie et al, Deciphering the message in protein sequences:Tolerance to amino acid substitution. Science, vol. 247, p1306–1310, 1990.

Houghten et al, Relative importance of position and individual amino acid residues in peptide antigen–antibody interactions:Implications in the mechanism of antigenic drift and antigenic shift. Vaccines 86, pp2125, 1986.

Pereira et al. The ontogeny of a 57–Kd cationic antimicrobial protein of human polyphonuclear leukocytes:Localization to a novel granule population., Blood vol., 76, pp 825–834, 1990.

Hovde et al , Characterization of a protein from normal human polymorphonuclear leukocytes with bactericidal activity against *Pseudomonas aeruginosa*, Infection and immunity, von 54, pp142–148, 1986.

Ooi et al, A 25 –Kda NH2–terminal fragment carries all the antibacterial activities of the human neutrophil 60–kDa bactericidal/permeability–increasing protein, J.Biological Chemistry, vol. 262, pp14891–14894, 1987.

BPI MUTAGENIC PRIMERS

C-TERMINAL TRUNCATION OF BPI

25KD Pro 212 TGA

```
AA.  205                          210        212
     Ile   Asn  Tyr  Gly  Leu  Val  Ala  Pro  Ter.Bam   HI  (SEQ ID NO: 1)

     TAG  AAC  TAT  GGT  CTG  GTG  GCA  CCT  TGA  GGATCCGCG  (SEQ ID NO: 2)
COMP
          3'    ATA  CCA  GAC  CAC  CGT  GGA  ACT  CCTAGGCGC 5'  (SEQ ID NO: 3)
OLIGO 459:
     5' CGCGGATCC    TCA  AGG  TGC  CAC  CAG  ACC  ATA  3'  (SEQ ID NO: 4)
```

FIG. 6

BPI MUTAGENIC PRIMERS

C-TERMINAL TRUNCATION OF BPI

38KD Pro 337 TGA

```
AA.  330                          335         337
     Pro  Thr  Gly  Leu  Thr  Phe  Tyr  Pro Ter    Bam HI  (SEQ ID NO: 5)
     CCC  ACC  GGC  CTT  ACC  TTC  TAC  CCT  TGA  GGATCCGCG  (SEQ ID NO: 6)
COMP:
          3' CCG   GAA  TGG  AAG  ATG  GGA  ACT  CCTAGGCGC 5'  (SEQ ID NO: 7)
OLIGO 460:
     5'   CGCGGATCC   TCA  AGG  GTA  GAA  GGT  AAG  GCC   3'  (SEQ ID NO: 8)
```

FIG. 7

BPI MUTAGENIC PRIMERS

C-TERMINAL TRUNCATION OF BPI

PREFFERED ATG 5'HIND III:

```
AA.       -31                         -26
      HINd III    Start      Met  Arg   Glu   Asn   Met   Arg  (SEQ ID NO: 9)
      CCCAAGCTT  GCC ACC   ATG   AGA   GAG   AAC   ATG   GCC   (SEQ ID NO: 10)
```

OLIGO 458:
5' CCCAAGCTT GCC ACC ATG AGA GAG AAC ATG GCC 3' (SEQ ID NO: 11)

AAAAAAACC CGAGATCCGCGGATC CTTTCCT (SEQ ID NO: 12)

AvaIXho2Sst2 BamHI

HUMAN BACTERIAL PROTEIN cDNA CLONING

```
                                       -30                                         -20
                                   met arg glu asn met ala arg gly pro cys asn ala pro arg trp val ser
  1 CAGGCCTTGAGGTTTTGGCAGCTCTGGAGG ATG AGA GAG AAC ATG GCC AGG GGC CCT TGC AAC GCG CCG AGA TGG GTG TCC

                -10                                       1                                10
    leu met val leu val ala ile gly thr ala val thr ala ala Val Asn Pro Gly Val Val Val Arg Ile Ser Gln
 82 CTG ATG GTG CTC GTC GCC ATA GGC ACC GCC GTG ACA GCG GCC GTC AAC CCT GGC GTC GTG GTC AGG ATC TCC CAG

                                20                         1        30
    Lys Gly Leu Asp Tyr Ala Ser Gln Gln Gly Thr Ala Ala Leu Gln Lys Glu Leu Lys Arg Ile Lys Ile Pro Asp
157 AAG GGC CTG GAC TAC GCC AGC CAG CAG GGG ACG GCC GCT CTG CAG AAG GAG CTG AAG AGG ATC AAG ATT CCT GAC

                40                                  50                                      60
    Tyr Ser Asp Ser Phe Lys Ile Lys His Leu Gly Lys Gly His Tyr Ser Phe Tyr Ser Met Asp Ile Arg Glu Phe
232 TAC TCA GAC AGC TTT AAG ATC AAG CAT CTT GGG AAG GGG CAT TAT AGC TTC TAC AGC ATG GAC ATC CGT GAA TTC

                                70                                  80
    Gln Leu Pro Ser Ser Gln Ile Ser Met Val Pro Asn Val Gly Leu Lys Phe Ser Ile Ser Asn Ala Asn Ile Lys
307 CAG CTT CCC AGT TCC CAG ATA AGC ATG GTG CCC AAT GTG GGC CTT AAG TTC TCC ATC AGC AAC GCC AAT ATC AAG
```

FROM FIG. 12A

```
                90                                          100                                                 110
    Ile Ser Gly Lys Trp Lys Ala Gln Lys Arg Phe Leu Lys Met Ser Gly Asn Phe Asp Leu Ser Ile Glu Gly Met
382 ATC AGC GGG AAA TGG AAG GCA CAA AAG AGA TTC TTA AAA ATG AGC GGC AAT TTT GAC CTG AGC ATA GAA GGC ATG

                                120                                     130
    Ser Ile Ser Ala Asp Leu Lys Leu Gly Ser Asn Pro Thr Ser Gly Lys Pro Thr Ile Thr Cys Ser Ser Cys Ser
457 TCC ATT TCG GCT GAT CTG AAG CTG GGC AGT AAC CCC ACG TCA GGC AAG CCC ACC ATC ACC TGC TCC AGC TGC AGC

                140                                         150                                     160
    Ser His Ile Asn Ser Val His Val His Ile Ser Lys Ser Lys Val Gly Trp Leu Ile Gln Leu PHe His Lys Lys
532 AGC CAC ATC AAC AGT GTC CAC GTG CAC ATC TCA AAG AGC AAA GTC GGG TGG CTG ATC CAA CTC TTC CAC AAA AAA

                            170                                             180
    Ile Glu Ser Ala Leu Arg Asn Lys Met Asn Ser Gln Val Cys Glu Lys Val Thr Asn Ser Val Ser Ser Lys Leu
607 ATT GAG TCT GCG CTT CGA AAC AAG ATG AAC AGC CAG GTC TGC GAG AAA GTG ACC AAT TCT GTA TCC TCC AAG CTG

                190                                         200                                     210  9
    Gln Pro Tyr Phe Gln Thr Leu Pro Val Met Thr Lys Ile Asp Ser Val Ala Gly Ile Asn Tyr Gly Leu Val Ala
682 CAA CCT TAT TTC CAG ACT CTG CCA GTA ATG ACC AAA ATA GAT TCT GTG GCT GGA ATC AAC TAT GGT CTG GTG GCA

                                220                         3                   230
    Pro Pro Ala Thr Thr Ala Glu Thr Leu Asp Val Gln Met Lys Gly Glu Phe Tyr Ser Glu Asn His His Asn Pro
757 CCT CCA GCA ACC ACG GCT GAG ACC CTG GAT GTA CAG ATG AAG GGG GAG TTT TAC AGT GAG AAC CAC CAC AAT CCA
```

FROM FIG. 12B

```
                    240                                2             250                                                    260
     Pro Pro Phe Ala Pro Pro Val Met Glu Phe Pro Ala Ala His Asp Arg Met Val Tyr Leu Gly Leu Ser Asp Tyr
832  CCT CCC TTT GCT CCA CCA GTG ATG GAG TTT CCC GCT GCC CAT GAC CGC ATG GTA TAC CTG GGC CTC TCA GAC TAC

                                    270                                         280
     Phe Phe Asn Thr Ala Gly Leu Val Tyr Gln Glu Ala Gly Val Leu Lys Met thr Leu Arg Asp Asp Met Ile Pro
907  TTC TTC AAC ACA GCC GGG CTT GTA TAC CAA GAG GCT GGG GTC TTG AAG ATG ACC CTT AGA GAT GAC ATG ATT CCA

                    290                                300                                          310
     Lys Glu Ser Lys Phe Arg Leu Thr Thr Lys Phe Phe Gly Thr Phe Leu Pro Glu Val Ala Lys Lys Phe Pro Asn
982  AAG GAG TCC AAA TTT CGA CTG ACA ACC AAG TTC TTT GGA ACC TTC CTA CCT GAG GTG GCC AAG AAG TTT CCC AAC

                                    320                                         330
     Met Lys Ile Gln Ile His Val Ser Ala Ser Thr Pro Pro His Leu Ser Val Gln Pro Thr Gly Leu Thr Phe Tyr
1057 ATG AAG ATA CAG ATC CAT GTC TCA GCC TCC ACC CCG CCA CAC CTG TCT GTG CAG CCC ACC GGC CTT ACC TTC TAC

                    340                                     350                                     360
     Pro Ala Val Asp Val Gln Ala Phe Ala Val Leu Pro Asn Ser Ser Leu Ala Ser Leu Phe Leu Ile Gly Met His
1132 CCT GCC GTG GAT GTC CAG GCC TTT GCC GTC CTC CCC AAC TCC TCC CTG GCT TCC CTC TTC CTG ATT GGC ATG CAC
```

FROM FIG. 12C

```
                                       370                                                           380
     Thr Thr Gly Ser Met Glu Val Ser Ala Glu Ser Asn Arg Leu Val Gly Glu Leu Lys Leu Asp Arg Leu Leu Leu
1207 ACA ACT GGT TCC ATG GAG GTC AGC GCC GAG TCC AAC AGG CTT GTT GGA GAG CTC AAG CTG GAT AGG CTG CTC CTG

                 390                                     400                                         410
     Glu Leu Lys His Ser Asn Ile Gly Pro Phe Pro Val Glu Leu Leu Gln Asp Ile Met Asn Tyr Ile Val Pro Ile
1282 GAA CTG AAG CAC TCA AAT ATT GGC CCC TTC CCG GTT GAA TTG CTG CAG GAT ATC ATG AAC TAC ATT GTA CCC ATT

                                 420                                     430
     Leu Val Leu Pro Arg Val Asn Glu Lys Leu Gln Lys Gly Phe Pro Leu Pro Thr Pro Ala Arg Val Gln Leu Tyr
1357 CTT GTG CTG CCC AGG GTT AAC GAG AAA CTA CAG AAA GGC TTC CCT CTC CCG ACG CCG GCC AGA GTC CAG CTC TAC

                 440                                     450                                     460
     Asn Val Val Leu Gln Pro His Gln Asn Phe Leu Leu Phe Gly Ala Asp Val Val Tyr Lys (SEQ ID NO: 13)
1432 AAC GTA GTG CTT CAG CCT CAC CAG AAC TTC CTG CTG TTC GGT GCA GAC GTT GTC TAT AAA TGA AGGCACCAGGGGTGCC

1511 GGGGGCTGTCAGCCGCACCTGTTCCTGATGGGCTGTGGGGCACCGGCTGCCTTTCCCCAGGGAATCCTCTCCAGATCTTAACCAAGAGCCCCTTGCAAAC

1611 TTCTTCGACTCAGATTCAGAAATGATCTAAACACGAGGAAACATTATTCATTGGAAAAGTGCATGGTGTGTATTTTAGGGATTATGAGCTTCTTTCAAGG

1711 GCTAAGGCTGCAGAGATATTTCCTCCAGGAATCGTGTTTCAATTGTAACCAAGAAATTTCCATTTGTGCTTCATGAAAAAAAACTTCTGGTTTTTTTCAT

1811 GTG---poly-A tail (SEQ ID NO: 14)
```

FIG. 12D

| | |
|---|---|
| -31 | M R E N M A R G P C N A P R W V S L M V L V A I G T A V T A |
| -1 | A V N P G V V V R I S Q K G L D Y A S Q Q G T A A L Q K E L |
| 30 | K R I K I P D Y S D S F K I K H L G K G H Y S F Y S M D I R |
| 60 | E F Q L P S S Q I S M V P N V G L K F S I S N A N I K I S G |
| 90 | K W K A Q K R F L K M S G N F D L S I E G M S I S A D L K L |
| 120 | G S N P T S G K P T I T C S S C S S H I N S V H V H I S K S |
| 150 | K V G W L I Q L F H K K I E S A L R N K M N S Q V C E K V T |
| 180 | N S V S S K L Q P Y F Q T L P V M T K I D S V A G I N Y G L |
| 210 | V A P P A T T A E T L D V Q M K G E F Y S E N H H N P P P F |
| 240 | A P P V M E F P A A H D R M V Y L G L S D Y F F N T A G L V |
| 270 | Y Q E A G V L K M T L R D D M I P K E S K F R L T T K F F G |
| 300 | T F L P E V A K K F P N M K I Q I H V S A S T P P H L S V Q |
| 330 | P T G L T F Y P (SEQ ID NO: 15) |

FIG. 13

-31 M R E N M A R G P C N A P R W V S L M V L V A I G T A V T A
-1 A V N P G V V V R I S Q K G L D Y A S Q Q G T A A L Q K E L
30 K R I K I P D Y S D S F K I K H L G K G H Y S F Y S M D I R
60 E F Q L P S S Q I S M V P N V G L K F S I S N A N I K I S G
90 K W K A Q K R F L K M S G N F D L S I E G M S I S A D L K L
120 G S N P T S G K P T I T C S S C S S H I N S V H V H I S K S
150 K V G W L I Q L F H K K I E S A L R N K M N S Q V C E K V T
180 N S V S S K L Q P Y F Q T L P V M T K I D S V A G I N Y G L
210 v A P (SEQ ID NO: 16)

FIG. 14

A. LBP/BPI Chimera

```
LBP->      10         20         30         40         50         60
ANPGLVARIT DKGLQYAAQE GLLALQSELL RITLPDFTGD LRIPHVGRGR YEFHSLNIHS
       70         80         90        100        110        120
CELLHSALRP VPGQGLSLSI SDSSIRVQGR WKVRKSFFKL QGSFDVSVKG ISISVNLLLG
      130        140        150        160        170        180
SESSGRPTGY CLSCSSDIAD VEVDMSGDSG WLLNLFHNQI ESKFQKVLES RICEMIQKSV
      190       BPI->   210        220        230        240
SSDLQPYLQT LPVTTEIDSV AGINYGLVAP PATTAETLDV QMKGEFYSEN HHNPPPFAPP
      250        260        270        280        290        300
VMEFPAAHDR MVYLGLSDYF FNTAGLVYQE AGVLKMTLRD DMIPKESKFR LTTKFFGTFL
      310        320        330        340        350        360
PEVAKKFPNM KIQIHVSAST PPHLSVQPTG LTFYPAVDVQ AFAVLPNSSL ASLFLIGMHT
      370        380        390        400        410        420
TGSMEVSAES NRLVGELKLD RLLLELKHSN IGPFPVELLQ DIMNYIVPIL VLPRVNEKLQ
      430        440        450
KGFPLPTPAR VQLYNVVLQP HQNFLLFGAD VVYK (SEQ ID NO: 17)
```

FIG. 23

B. CHO⁻ BPI

| 10 | 20 | 30 | 40 | 50 | 60 |
|---|---|---|---|---|---|
| VNPGVVVRIS | QKGLDYASQQ | GTAALQKELK | RIKIPDYSDS | FKIKHLGKGH | YSFYSMDIRE |
| 70 | 80 | 90 | 100 | 110 | 120 |
| FQLPSSQISM | VPNVGLKFSI | SNANIKISGK | WKAQKRFLKM | SGNFDLSIEG | MSISADLKLG |
| 130 | 140 | 150 | 160 | 170 | 180 |
| SNPTSGKPTI | TCSSCSSHIN | SVHVHISKSK | VGWLIQLFHK | KIESALRNKM | NSQVCEKVTN |
| 190 | 200 | 210 | 220 | 230 | 240 |
| SVSSKLQPYF | QTLPVMTKID | SVAGINYGLV | APPATTAETL | DVQMKGEFYS | ENHHNPPPFA |
| 250 | 260 | 270 | 280 | 290 | 300 |
| PPVMEFPAAH | DRMVYLGLSD | YFFNTAGLVY | QEAGVLKMTL | RDDMIPKESK | FRLTTKFFGT |
| 310 | 320 | 330 | 340 | 350 | 360 |
| FLPEVAKKFP | NMKIQIHVSA | STPPHLSVQP | TGLTFYPAVD | VQAFAVLPNS | ALASLFLIGM |
| 370 | 380 | 390 | 400 | 410 | 420 |
| HTTGSMEVSA | ESNRLVGELK | LDRLLLELKH | SNIGPFPVEL | LQDIMNYIVP | ILVLPRVNEK |
| 430 | 440 | 450 | | | |
| LQKGFPLPTP | ARVQLYNVVL | QPHQNFLLFG | ADVVYK (SEQ ID NO: 18) | | |

FIG. 24

C. BPI (DP linkage)

```
        10         20         30         40         50         60
VNPGVVVRIS QKGLDYASQQ GTAALQKELK RIKIPDYSDS FKIKHLGKGH YSFYSMDIRE
        70         80         90        100        110        120
FQLPSSQISM VPNVGLKFSI SNANIKISGK WKAQKRFLKM SGNFDLSIEG MSISADLKLG
       130        140        150        160        170        180
SNPTSGKPTI TCSSCSSHIN SVHVHISKSK VGWLIQLFHK KIESALRNKM NSQVCEKVTN
       190        200        210        220        230        240
SVSSKLQPYF QTLPVMTKID PVAGINYGLV APPATTAETL DVQMKGEFYS ENHHNPPPFA
       250        260        270        280        290        300
PPVMEFPAAH DRMVYLGLSD YFFNTAGLVY QEAGVLKMTL RDDMIPKESK FRLTTKFFGT
       310        320        330        340        350        360
FLPEVAKKFP NMKIQIHVSA STPPHLSVQP TGLTFYPAVD VQAFAVLPNS SLASLFLIGM
       370        380        390        400        410        420
HTTGSMEVSA ESNRLVGELK LDRLLLELKH SNIGPFPVEL LQDIMNYIVP ILVLPRVNEK
       430        440        450
LQKGFPLPTP ARVQLYNVVL QPHQNFLLFG ADVVYK (SEQ ID NO: 19)
```

FIG. 25

BPI cDNA Reengineering

```
                        NheI
Oligo #98 -> TATCATGCTAG- (SEQ ID NO: 20)
        -CAG GCC TTG AGG TTT TGG CAG  (SEQ ID NO: 21)
   1    CAG GCC TTG AGG TTT TGG CAG CTC TGG AGG ATG AGA GAG AAC ATG GCC     48
   1                                            Met Arg Glu Asn Met Ala      6

  49    AGG GGC CCT TGC AAC GCG CCG AGA TGG GTG TCC CTG ATG GTG CTC GTC     96
   7    Arg Gly Pro Cys Asn Ala Pro Arg Trp Val Ser Leu Met Val Leu Val     22

            ... 25K ...

 625    AAC AAG ATG AAC AGC CAG GTC TGC GAG AAA GTG ACC AAT TCT GTA TCC    672
 199    Asn Lys Met Asn Ser Gln Val Cys Glu Lys Val Thr Asn Ser Val Ser    214
                                                                ClaI
                                            CTG CCA GTA ATG ACC AAA ATC
                              Oligo #89 ->  CTG CCA GTA ATG ACC AAA ATC (SEQ ID NO: 27)
 673    TCC AAG CTG CAA CCT TAT TTC CAG ACT CTG CCA GTA ATG ACC AAA ATA    720
 215    Ser Lys Leu Gln Pro Tyr Phe Gln Thr Leu Pro Val Met Thr Lys Ile    230

        GAT GCT GTG GCT GGA ATC <- Oligo #93 (SEQ ID NO: 22)
        GAT TCT GTG GCT GGA ATC <- Oligo #90 (SEQ ID NO: 23)
 721    GAT TCT GTG GCT GGA ATC AAC TAT GGT CTG GTG GCA CCT CCA GCA ACC    768
 231    Asp Ser Val Ala Gly Ile Asn Tyr Gly Leu Val Ala Pro Pro Ala Thr    246

 769    ACG GCT GAG ACC CTG GAT GTA CAG ATG AAG GGG GAG TTT TAC AGT GAG    816
 247    Thr Ala Glu Thr Leu Asp Val Gln Met Lys Gly Glu Phe Tyr Ser Glu    262

            ... 30K ...
                                                     GT CTG CAA CAG ATA
1441    CTT CAG CCT CAC CAG AAC TTC CTG CTG TTC GGT GCA GAC GTT GTC TAT   1488
 471    Leu Gln Pro His Gln Asn Phe Leu Leu Phe Gly Ala Asp Val Val Tyr    486

                XhoI
        TTT ACT TGAGCTCATGCAG <- Oligo #97 (SEQ ID NO: 24)
1489    AAA TGA AGG CAC CAG GGG TGC CGG GGG CTG TCA GCC GCA CCT GTT CCT   1536
 487    Lys *** (SEQ ID NO: 25)                                            488

1537    GAT GGG CTG TGG GGC ACC GGC TGC CTT TCC CCA GGG AAT CCT CTC CAG   1584
                                                      (SEQ ID NO: 26)
```

FIG. 26

RECOMBINANT ANALOGS OF BACTERICIDAL/PERMEABILITY INCREASING PROTEIN

This application is a continuation of U.S. application Ser. No. 07/915,720, filed Jul. 22, 1992, now U.S. Pat. No. 5,770,694, issued Jun. 23, 1998, which is a national phase of PCT/US91/05758, filed Aug. 13, 1991, which is a continuation-in-part of U.S. application Ser. No. 07/681,551, filed April 5, 1991, now U.S. Pat. No. 5,171,739, issued Dec. 15, 1992, which is a continuation-in-part of U.S. application Ser. No. 07/567,016, filed Aug. 13, 1990, now abandoned, which is a continuation-in-part of U.S. application Ser. No. 07/468,696, filed Jan. 22, 1990, now U.S. Pat. No. 5,089,274, issued Feb. 18, 1992, which is a continuation-in-part of U.S. application Ser. No. 07/310,842, filed Feb. 14, 1989, now abandoned, the contents of which are hereby incorporated by reference.

BACKGROUND OF THE INVENTION

Gram negative infections are a major cause of morbidity and mortality especially, in hospitalized and immunocompromised patients. [Duma, R. J., Am. J. of Med., 78 (Suppl. 6A): 154–164 (1985); and Kreger B. E., D. E. Craven and W. R. McCabe, Am. J. Med., 68: 344–355 (1980)]. Although available antibiotics are generally effective in containing the infection, they do nothing to neutralize the pathophysiological effects associated with lipopolysaccharide (LPS).

LPS is a major component of the outer membrane of gram negative bacteria and is released when the organisms are lysed. [Shenep, J. L. and K. A. Morgan, J. Infect. Dis., 150 (3): 380–388 (1984)]

LPS released during antibiotic therapy is a potent stimulator of the inflammatory response. Many detrimental effects of LPS in vivo result from soluble mediators released by inflammatory cells. [Morrison D. C. and R. J. Ulevich, Am. J. Pathol., 93 (2): 527–617 (1978)] LPS induces the release of mediators by host inflammatory cells which may ultimately result in disseminated intravascular coagulation (DIC), adult respiratory distress syndrome (ARDS), cardiac dysfunction, organ failure, liver failure (hepatobiliary dysfunction), brain failure (CNS dysfunction), renal failure, multi-organ failure and shock.

Soluble LPS causes decreased neutrophil chemotaxis, increased adhesiveness, elevated hexose monophosphate shunt activity and $O_2$ radical production, upregulation of surface receptors for complement, and release of granule proteins into the surrounding medium. [Morrison and Ulevich (1978)]

Endotoxemia is a condition associated with the presence of endotoxins, i.e. heat stable bacterial toxins, in the blood. Endotoxins elicit an inflammatory response that is beneficial in fighting the infection but can be damaging to the host if uncontrolled. Endotoxemia induces, production of endotoxin binding proteins from the liver and causes release of microbicidal proteins from leukocytes. Our studies show that one of these leukocytes proteins, i.e. BPI, previously known only for its bactericidal activity in vitro, inhibits the ability of endotoxin to stimulate neutrophils and monocytes in vitro and reduces death due to endotoxin or bacterial challenge when given in vivo. Further, BPI has been shown to possess antibiotic functions but not cytotoxin functions against the host cell.

Monocytes and neutrophilic granulocytes play a key role in host defense against bacterial infections and also participate in the pathology of endotoxemia. These cells ingest and kill microorganisms intracellularly and also respond to endotoxin in vivo and in vitro by releasing soluble proteins with microbicidal, proteolytic, opsonic, pyrogenic, complement activating and tissue damaging effects.

Tumor necrosis factor (TNF), a cytokine released by endotoxin stimulated monocytes mimics some of the toxic effects of endotoxin in vivo. Injecting animals with TNF causes fever, shock and alterations in glucose metabolism. TNF is also a potent stimulator of neutrophils. Other cytokines such as IL-1, IL-6, and IL-8 also mediate some of the pathophysiologic effects of LPS.

Despite improvements in antibiotic therapy, morbidity and mortality associated with endotoxemia remains high. Antibiotics alone are not effective in neutralizing the toxic effects of LPS. Therefore, the need arises for a therapy with direct endotoxin neutralizing activity. Current methods for treatment of endotoxemia use antibiotics and supportive care. Most available adjunct therapies treat symptoms of endotoxic shock such as low blood pressure and fever but do not inactivate endotoxin. Other therapies inhibit inflammatory host responses to LPS. As indicated below, present therapies have major limitations due to toxicity, immunogenicity, or in producible efficacy between animal models and human trials.

Polymyxin B (PMB) is a basic polypeptide antibiotic which has been shown to bind to, and structurally disrupt, the most toxic and biologically active component of endotoxin, Lipid A. PMB has been shown to inhibit endotoxin activation of neutrophil granule release in vitro and is a potential treatment for gram negative infections in humans. However, because of its systemic toxicity, this drug has limited use except as a topical agent.

Combination therapy using antibiotics and high doses of methylprednisolone sodium succinate (MPSS) has been shown to prevent death in an experimental model of gram negative sepsis using dogs. Another study using MPSS with antibiotics in a multicenter, double blind, placebo-controlled, clinical study in 223 patients with clinical signs of systemic sepsis concluded that mortality was not significantly different between the treatment and placebo groups. Further, the investigators found that resolution of secondary infection within 14 days was significantly higher in the placebo group.

A relatively new approach to treatment of endotoxemia is passive immunization with endotoxin neutralizing antibodies. Hyperimmune human immunoglobulin against *E. Coli* J5 has been shown to reduce mortality in patients with gram negative bacteremia and shock by 50%. Other groups have shown promising results in animal models using mouse, chimeric, and human monoclonal antibodies. Although monoclonal antibodies have advantages over hyperimmune sera, e.g. more consistent drug potency and decreased transmission of human pathogens, there are still many problems associated with administering immunoglobulin to neutralize LPS. Host responses to the immunoglobulins themselves can result in hypersensitivity. Tissue damage following complement activation and deposition of immune complexes is another concern in the use of therapies involving anti-endotoxin antibodies in septic patients.

BPI is a neutrophil granule protein first discovered in 1975 [Weiss, J., R. C. Franson, S. Becherdite, K. Schmeidler, and P. Elsbach J. Clin. Invest., 55:33 (1975)]. BPI was obtained in highly purified form from human neutrophils in 1978 and was shown to increase membrane permeability and have bactericidal activity against Gram negative bacteria when assayed in phosphate buffered saline in vitro [Weiss, J., et al. J. Biol. Chem, 253 (8): 2664–2672 (1:78)]. Weiss et al. [J. Biol. Chem. 254 (21): 110010–11014 (1979)], further showed that BPI increased phospholipase A2 activity suggesting a proinflammatory activity for BPI in addition to its in vitro bactericidal activity.

Rabbit BPI was purified in 1979 [Elsbach et al. J. Biol. Chem 254 (21): 11000–11009] and shown to have identical bactericidal and permeability increasing properties as BPI from humans providing a further source of material for study. Both BPI from rabbit and human were shown to be effective against a variety of Gram negative bacteria in vitro, including K1-encapsulated *E. coli* [*Weiss et al. Infection and Immunity* 38 (3): 1149–1153, (1982)].

A role for lipopolysaccharide in the in vitro bactericidal action of BPI was proposed in 1984 by Weiss et al. [J. Immunol. 132 (6): 3109–3115, (1984)]. These investigators demonstrated that BPI bound to the outer membrane of gram-negative bacteria, caused extracellular release of LPS, and selectively. Stimulated LPS biosynthesis. In 1984 a protein with similar properties was isolated from human neutrophils and designated cationic antimicrobial protein 57 (CAP 57) [Shafer, W. M., C. E. Martin and J. K. Spitznagel, Infect. Immun., 45:29 (1984)]. This protein is identical to BPI as determined by the N-terminal amino acid sequence, amino acid composition, molecular weight and source [Spitznagel et al., Blood 76:825–834, 1990]. Another group, Hovde and Gray, reported a bactericidal glycoprotein with virtually identical properties to BPI in 1986 [Hovde and Gray, Infection and Immunity 54 (1): 142–148 (1986)].

In 1985 Ooi et al. reported that BPI retains its in vitro bactericidal activity after cleavage with neutrophil proteases suggesting that fragments of the molecule retain activity (Ooi and Elsbach, Clinical Research 33 (2):567A (1985)]. All of the in vitro bactericidal and permeability increasing activities of BPI were present in the N-terminal 25 kD fragment of the protein [Ooi, C. E., et al. J. Biol. Chem. 262: 14891 (1987)]

Evidence that BPI binds to a structure associated with endotoxin on the outer membrane of bacteria is as follows: (1) increased sensitivity of rough strains of *E. coli* relative to smooth strains to the permeability increasing activities of BPI [Weiss, J. et al. Infect. Immun. 51:594 (1986)]; (2) the Prm A mutation which results in altered endotoxin structure caused decreased binding of both polymyxin B. and BPI [Farley, M. M. et al. Infect. Immun. 56:1536–1539 (1987) and Farley et al. Infect. Immun. 58:1589–1592 (1988)]; (3) polymyxin B (PMB) competed with BPI for binding to *S. typhimurium* [Farley 1988]; and (4) BPI shared amino acid sequence homology and immunocrossreactivity to another endotoxin binding protein termed Lipopolysaccharide Binding Protein (LBP) [Tobias et al., J. Biol. Chem. 263 (27): 13479–13481 (1988)].

LBP-LPS complexes bind to a cell surface receptor on monocytes (CD 14) which results in increased synthesis and release of the inflammatory cytokine tumor necrosis factor (TNF) [Schumann et al. Science 249:1429–1431. ]Thus, LBP promotes the immunostimulatory activities of LPS. BPI has exactly the opposite effect of LBP. BPI binds LPS and inhibits neutrophil and monocyte activation [Marra et al., J. Immunol. 144:662–666 (1990); Marra and Scott, WO90/09183, published Aug. 23, 1990; C. J. Fisher et al. Circulatory Shock 34: 120 (1991)].

A cDNA encoding BPI was obtained and sequenced by Gray et al. [Gray et al. Clin. Res. 36:620A (19 8) and Gray et al. J. Biol. Chem. 264 (16): 9505–9506 (1989)]. They reported that BPI is a membrane protein which can be cleaved and released in soluble form as a 25 kDa fragment.

BPI binding to gram negative bacteria was reported originally to disrupt LPS structure, alter microbial permeability to small hydrophobic molecules and cause cell death (Weiss, et al., 1978). More recently these same authors have demonstrated that such effects occur only in the absence of serum albumin. BPI has no bactericidal activity when added to bacteria cultured in the presence of serum albumin, thus suggesting that BPI does not kill bacteria in vivo where albumin is ubiquitous [Mannion et al. J. Clin. Invest. 85: 853–860 (1990) and Mannion et al J. Clin. Invest. 86: 631–641)]. Thus it has been previously understood in the art that the beneficial effects of BPI are limited to in vitro bactericidal effects.

Here we show that BPI binds endotoxin in the presence of serum and plasma and, unlike other known endotoxin binding proteins such as LBP, BPI inhibits the immunostimulatory and toxic activities of endotoxin both in vitro and in vivo respectively. Thus BPI has a novel and distinct use in the therapeutic and prophylactic treatment of endotoxin-related disorders including endotoxemia and endotoxic shock.

Further, BPI is described by Gray et al. [J. Biol. Chem. 264 (16): 9505–9509 (1989)] as a membrane protein which must be cleaved to the 25 kDa fragment to be released from the neutrophil granule membrane in soluble form. The present invention provides for a method of producing full length soluble BPI in active form. Further the present invention separates for the first time two molecular forms of the molecule apparently unresolved by Gray et al. representing glycosylated and nonglycosylated forms of the molecule which appear to have different serum half-life profiles in vivo and thus different therapeutic potential. BPI from neutrophils is a mixture of the glycoslyated and nonglycosylated forms.

SUMMARY OF THE INVENTION

The present invention provides a composition comprising a BPI Protein and an anionic compound which composition exhibits (1) no bactericidal activity and (2) endotoxin neutralizing activity.

This invention also provides a biologically active variant of BPI which (1) specifically binds to endotoxin, (2) competes with BPI Protein for binding to endotoxin, and (3) inhibits endotoxin-induced lethality.

The present invention further provides a method for producing and secreting a recombinant BPI Protein from a cell. This method comprises (a) constructing a vector comprising DNA encoding BPI Protein; (b) transfecting the cell with the vector; and (c) culturing the cell so transfected in culture medium under conditions such that recombinant BPI Protein is secreted.

Also, the present invention provides a method for producing a recombinant BPI Protein from a bacterial cell. This method comprises (a) constructing a vector without a signal sequence and comprising DNA encoding BPI Protein; (b) transfecting the bacterial cell with the vector; and (c) culturing the bacterial cell so transfected in culture medium under conditions such that recombinant BPI Protein is produced.

The subject invention further provides a method for producing a recombinant BPI Protein from an insect cell. This method comprises (a) constructing a vector comprising DNA encoding BPI Protein; (b) transfecting the insect cell with the vector; and (c) culturing the insect cell so transfected in culture medium under conditions such that BPI Protein is produced.

Also, this invention provides a method for determining the amount of endotoxin in a sample from a subject which comprises contacting the sample with a BPI Protein under conditions such that an endotoxin-BPI Protein complex is formed, detecting the amount of the complex so formed thereby determining the amount of endotoxin in the sample.

Additionally, the present invention provides a method for determining the amount of endotoxin in a sample containing bound and unbound endotoxin from a subject. This method comprises (a) treating the sample so as to denature any endotoxin binding protein to which the endotoxin may be bound thereby obtaining unbound endotoxin; (b) contacting the treated sample with a BPI Protein under conditions such that the BPI Protein binds to unbound endotoxin of step (a) so that a endotoxin-BPI Protein complex is formed; (c) detecting the amount of the complex so formed thereby determining the amount of endotoxin in the sample.

This present invention also provides a method of detecting endotoxin in a sample which comprises contacting the sample with a BPI Protein such that the endotoxin binds to the BPI Protein and forms a complex therewith; and detecting such complex.

The present invention further provides a method for coating a surgical tool with a BPI Protein so that the BPI Protein will complex with endotoxin which method comprises attaching BPI Protein onto a surface of the tool which surface is designed for contact with a biological sample.

Also, this invention provides a method for coating an implantable, invasive device with a BPI Protein so that it will form a complex with endotoxin which method comprises attaching BPI Protein onto a surface of the device which surface is designed for contact with a biological sample.

The present invention further provides a method for decontaminating a fluid containing endotoxin prior to administration of the fluid into a subject which comprises contacting the fluid with BPI Protein prior to administration, under conditions such that endotoxin forms a complex with BPI Protein, thereby decontaminating the fluid. The fluid may be blood, plasma, blood serum, an isotonic solution, a pharmaceutical agent, a cell culture reagent, or bone marrow.

This invention also provides a kit for detecting the presence of BPI Protein in a biological fluid sample which comprises (a) an assay buffer containing polymyxin B which binds unbound endotoxin molecules; (b) a first antibody attached to a surface, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody in assay buffer, an active BPI Protein contained in the biological fluid sample is bound by the first and second antibody thus forming a first antibody-BPI Protein-second antibody complex, detecting such complex, and thereby detecting BPI Protein in the biological fluid sample.

Also, this invention provides a kit for determining the amount of BPI Protein in a biological fluid sample which comprises (a) an assay buffer containing polymyxin B which binds unbound endotoxin molecules; (b) a first antibody attached to a surface, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody in assay buffer, an active BPI Protein contained in the biological fluid sample is bound by the first and second antibody thus forming a first antibody-active BPI Protein-second antibody complex, detecting such complex, and determining the amount of active BPI Protein in the biological fluid sample.

Additionally, this invention provides a method for preventing endotoxemia in a subject which comprises administering to the subject an amount of a BPI Protein effective to bind to endotoxin so as to prevent endotoxemia in the subject.

The present invention provides a method for treating a subject suffering from endotoxemia which comprises administering to the subject an amount of a BPI Protein effective to bind endotoxin so as to treat the subject suffering from endotoxemia.

A. pT7BPI-F (+) contains the full-length BPI Protein sequence (including the signal sequence) placed in the correct orientation behind the T7 promoter for expression.

B. pT7BPI-F (−) contains the full-length BPI Protein sequence (including the signal sequence) placed in the incorrect orientation behind the T7 promoter (resulting protein is a fusion protein with the 260 amino acid leader peptide of T7 gene 10).

C. pT7BPI-S contains the full-length BPI Protein sequence (without the signal sequence) placed in the correct orientation behind the T7 promoter for expression.

D. pT7212-F contains the proline-212 truncated BPI Protein sequence (including the signal sequence) placed in the correct orientation behind the T7 promoter for expression.

E. pT7212-S contains the proline-212 truncated BPI Protein sequence (without the signal sequence) placed in the correct orientation behind the T7 promoter for expression.

Figure 1A:
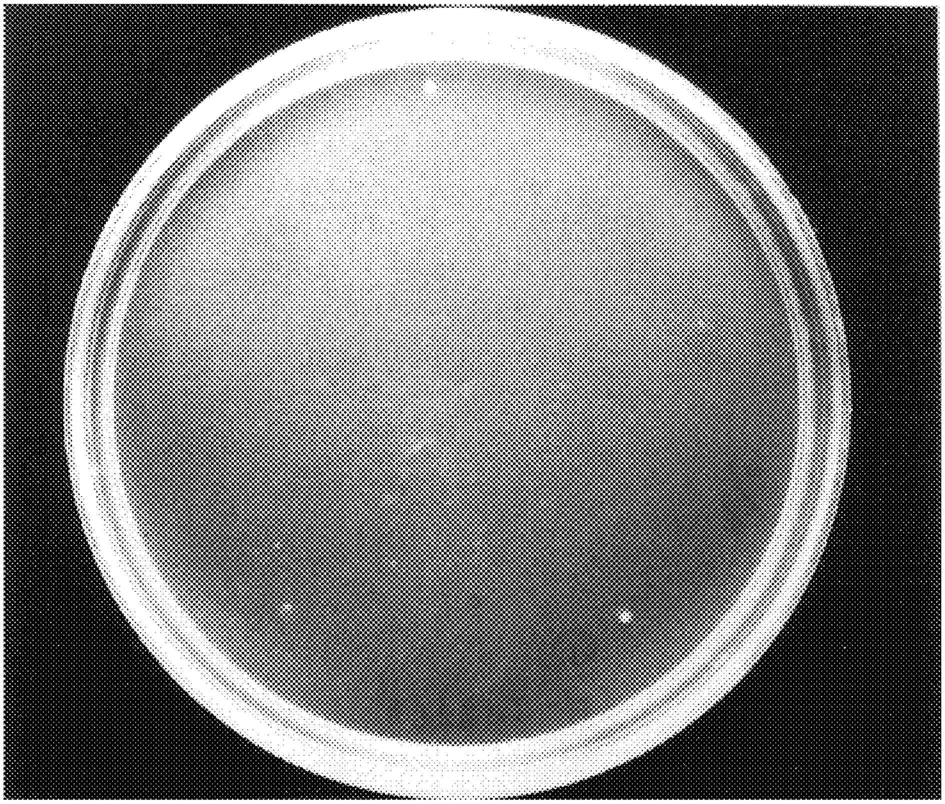
FIG. 1: Photographs of transformed plates of JM109 (DE3) with the T7 promoter/BPI Protein plasmid constructs. Photographs were taken with f8 at 1/125 second exposure.
Figure 1B:
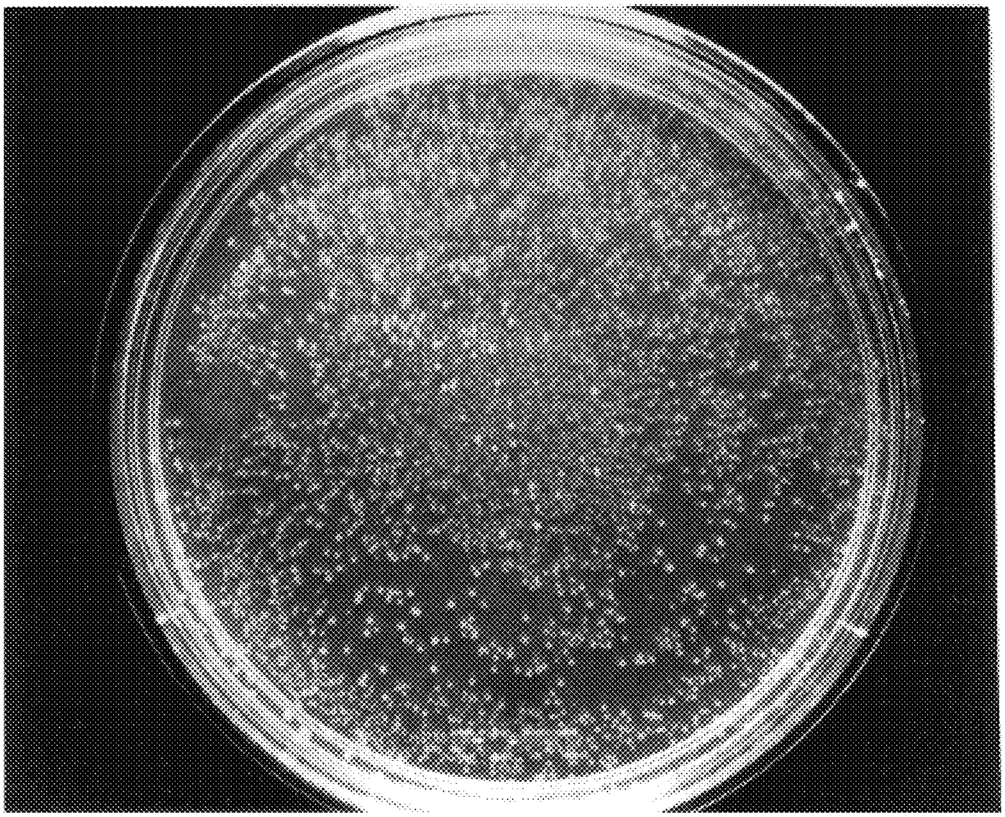
Figure 1C:
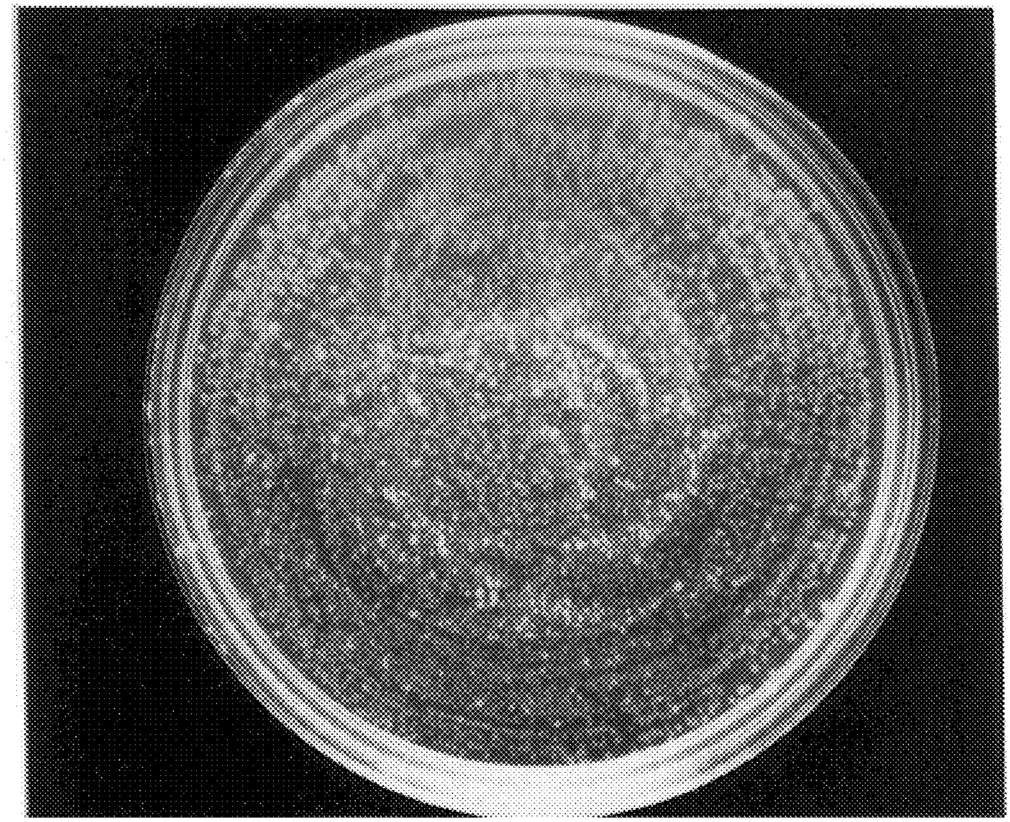
Figure 1D:
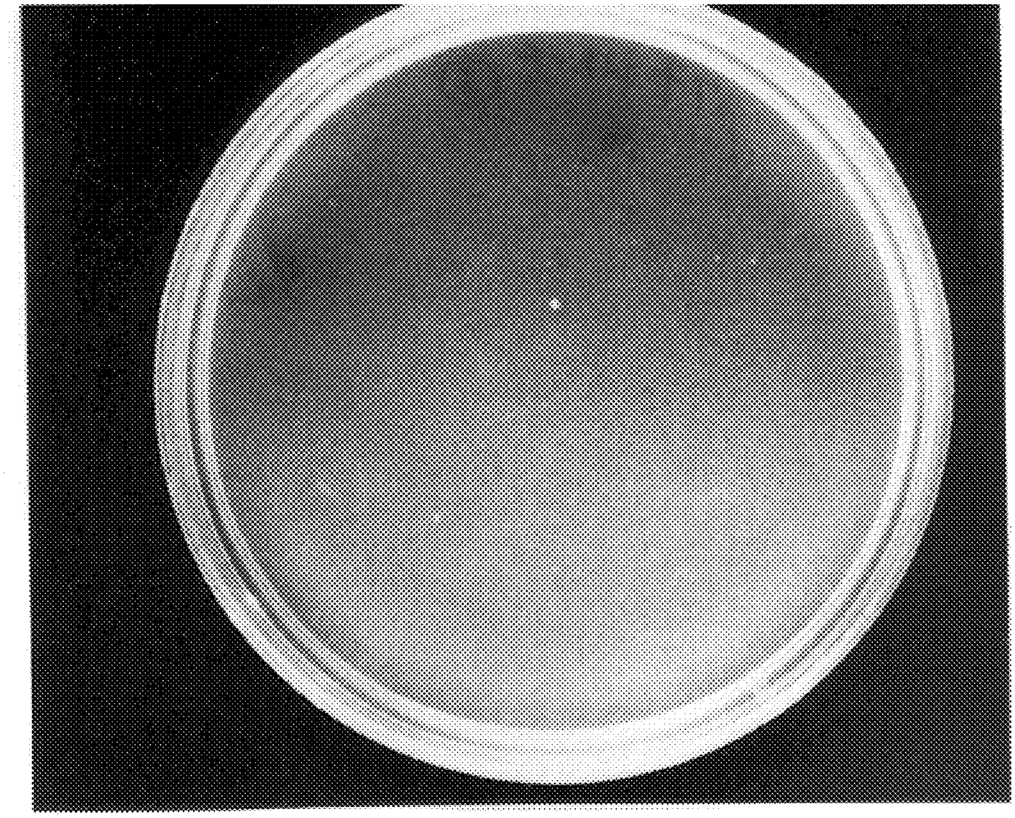
Figure 1E:
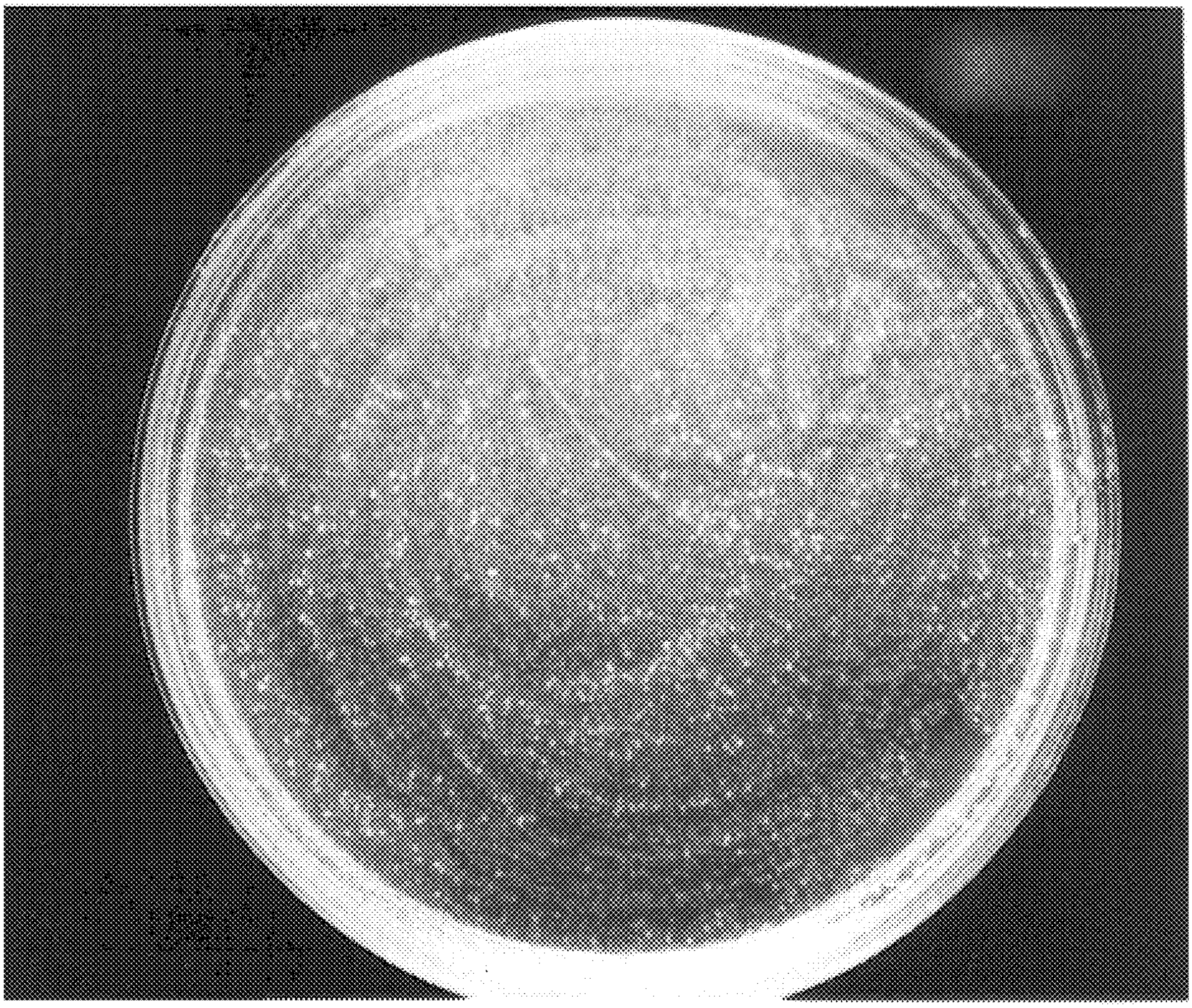
Figure 2:
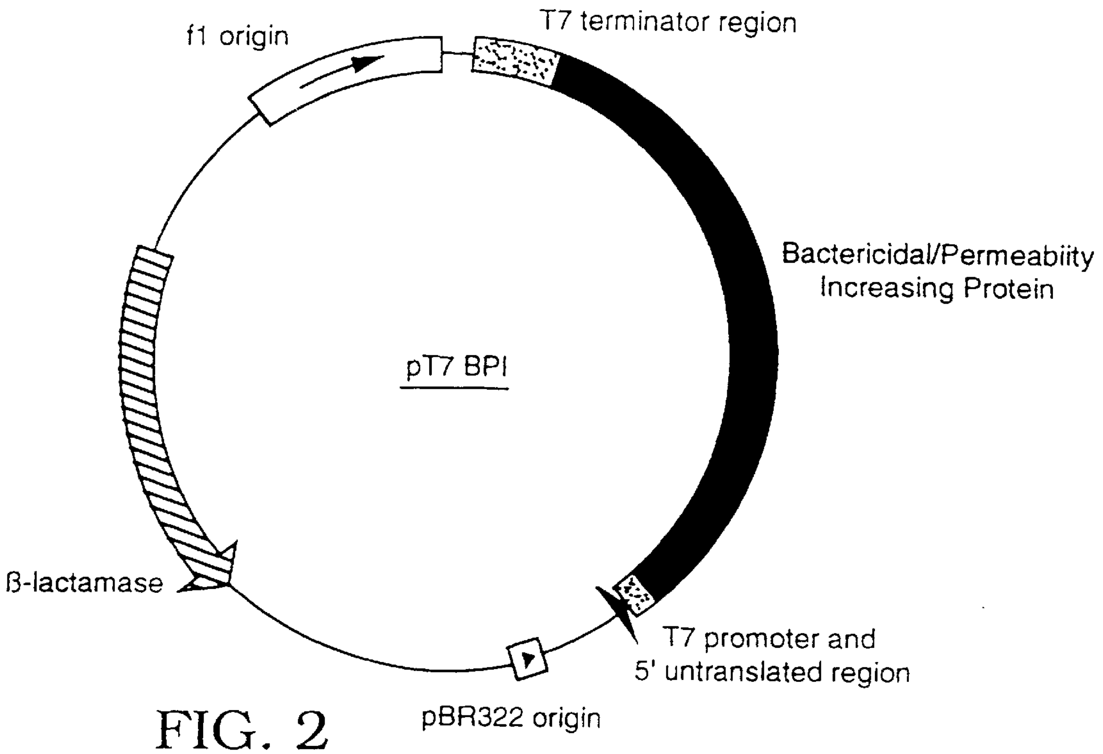

FIG. 2: Schematic of the pT7BPI Protein plasmid construct.

Figure 3:
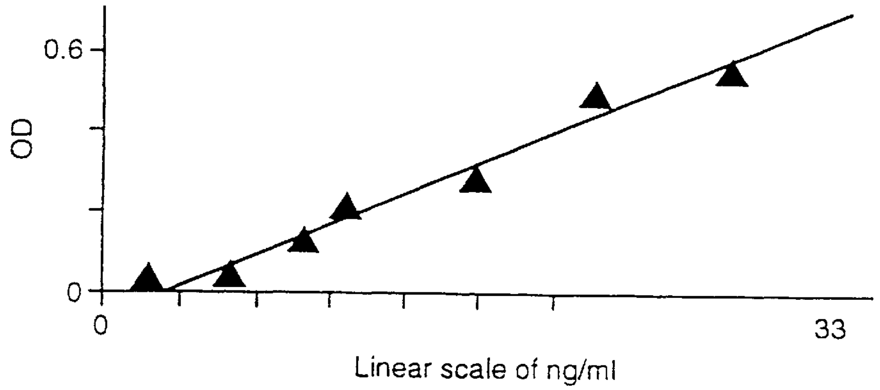

FIG. 3: Standard curve showing BPI Protein activity in ELISA Assay.

Figure 4:
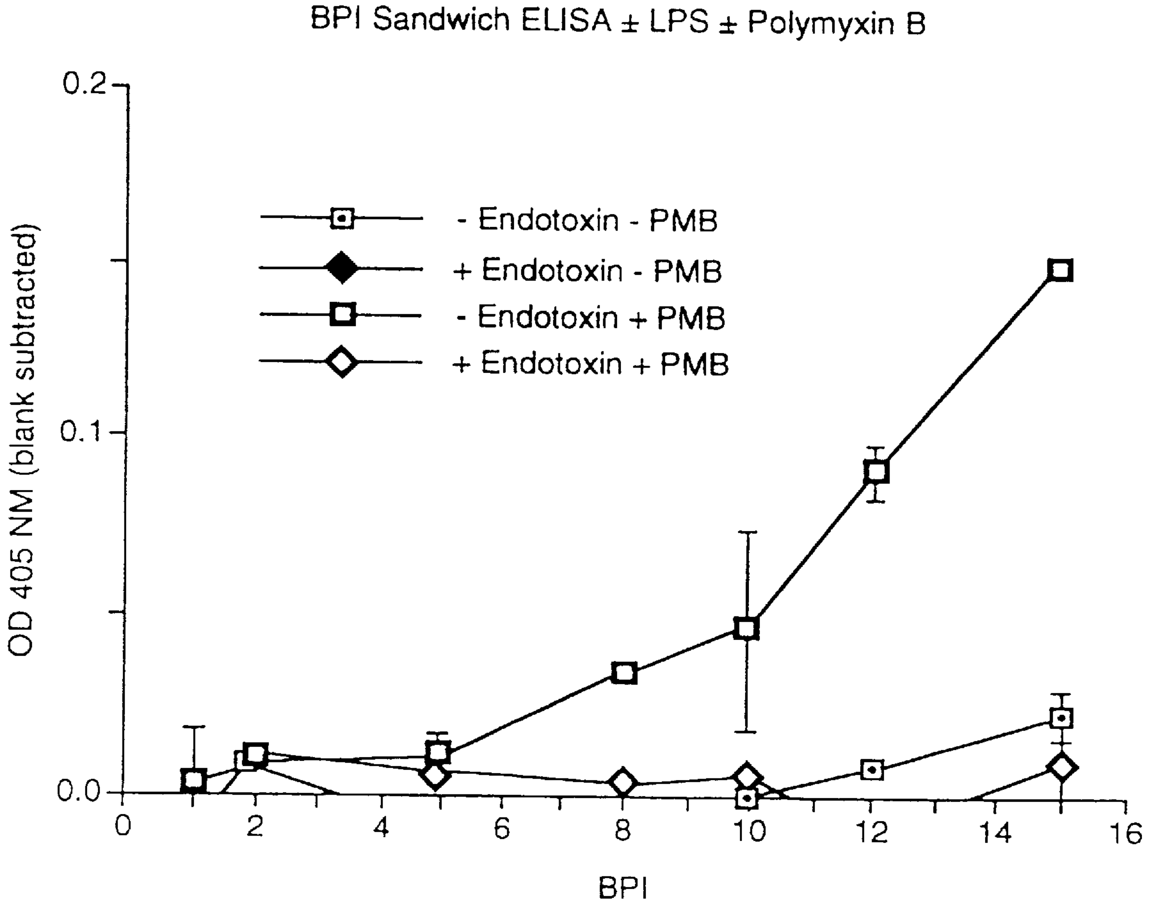

FIG. 4: BPI Protein Sandwich ELISA±endotoxin±Polymyxin B. The protocol is as follows: the BPI Protein Sandwich ELISA was performed in the presence and absence of 1 μg/ml of polymyxin B sulfate and the presence or absence of 1 μg/ml *E. coli* 0111 B4 endotoxin using PBS+1% BSA as diluent.

Figure 5:
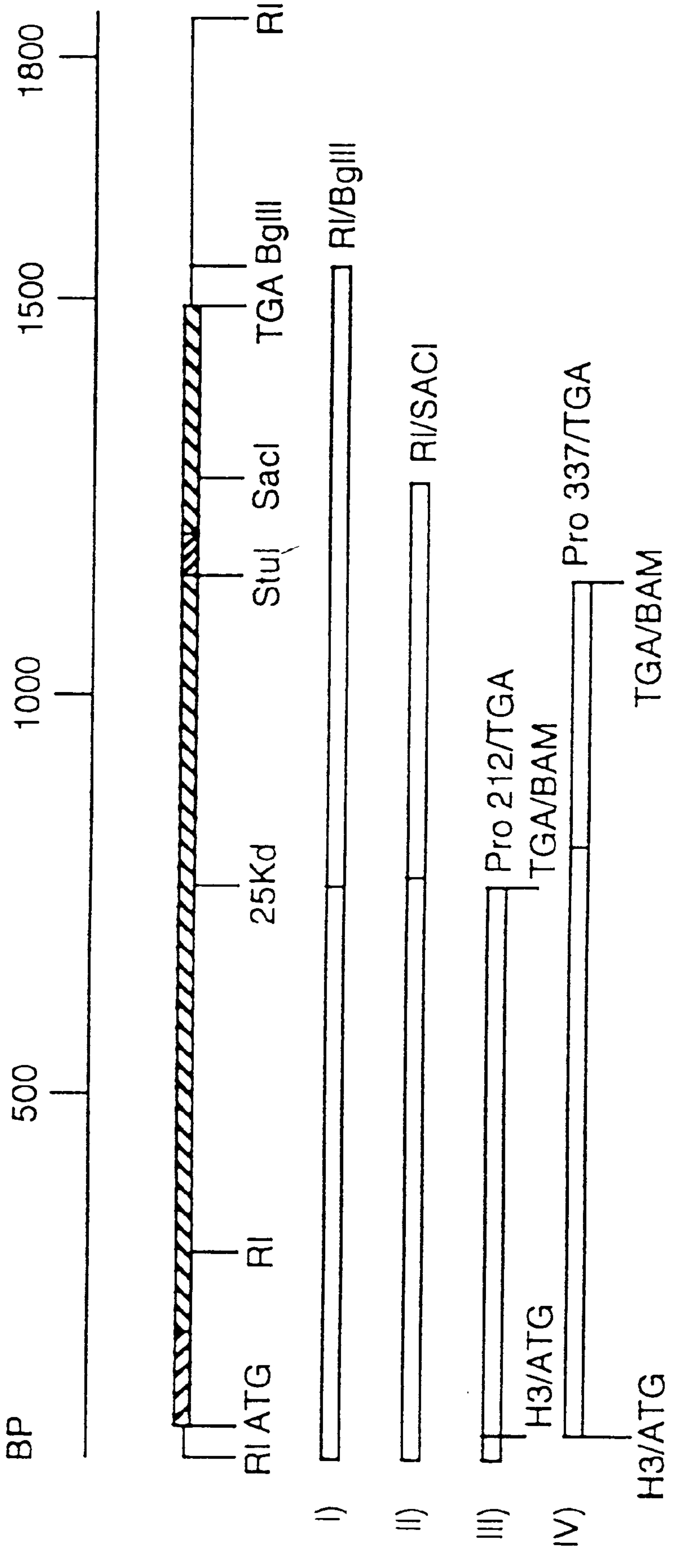

FIG. 5: Schematic drawing of cDNA encoding BPI.

FIG. 6: A nucleotide (SEQ ID NO: 2) and amino acid (SEQ ID NO: 1) sequence of BPI Protein mutagenic primer 25 kDa Pro 212 TGA which is a C-terminal truncation of BPI Protein.

FIG. 7: A nucleotide (SEQ ID NO: 6) and amino acid (SEQ ID NO: 5) sequence of BPI Protein mutagenic primer 38 kDa Pro 337 TGA which is a C-terminal truncation of BPI Protein.

FIG. 8: A nucleotide (SEQ ID NO: 10) and amino acid (SEQ ID NO: 9) sequence of BPI Protein mutagenic primer: Preferred ATG 5' HindIII which is a C-terminal truncation of BPI Protein.

Figure 9:
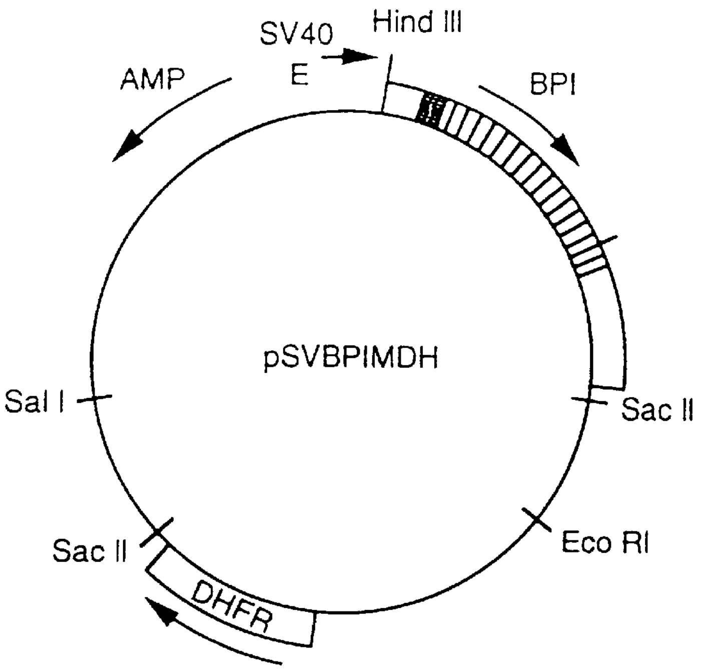

FIG. 9: A schematic drawing of pSVBPIMDH.

Figure 10:
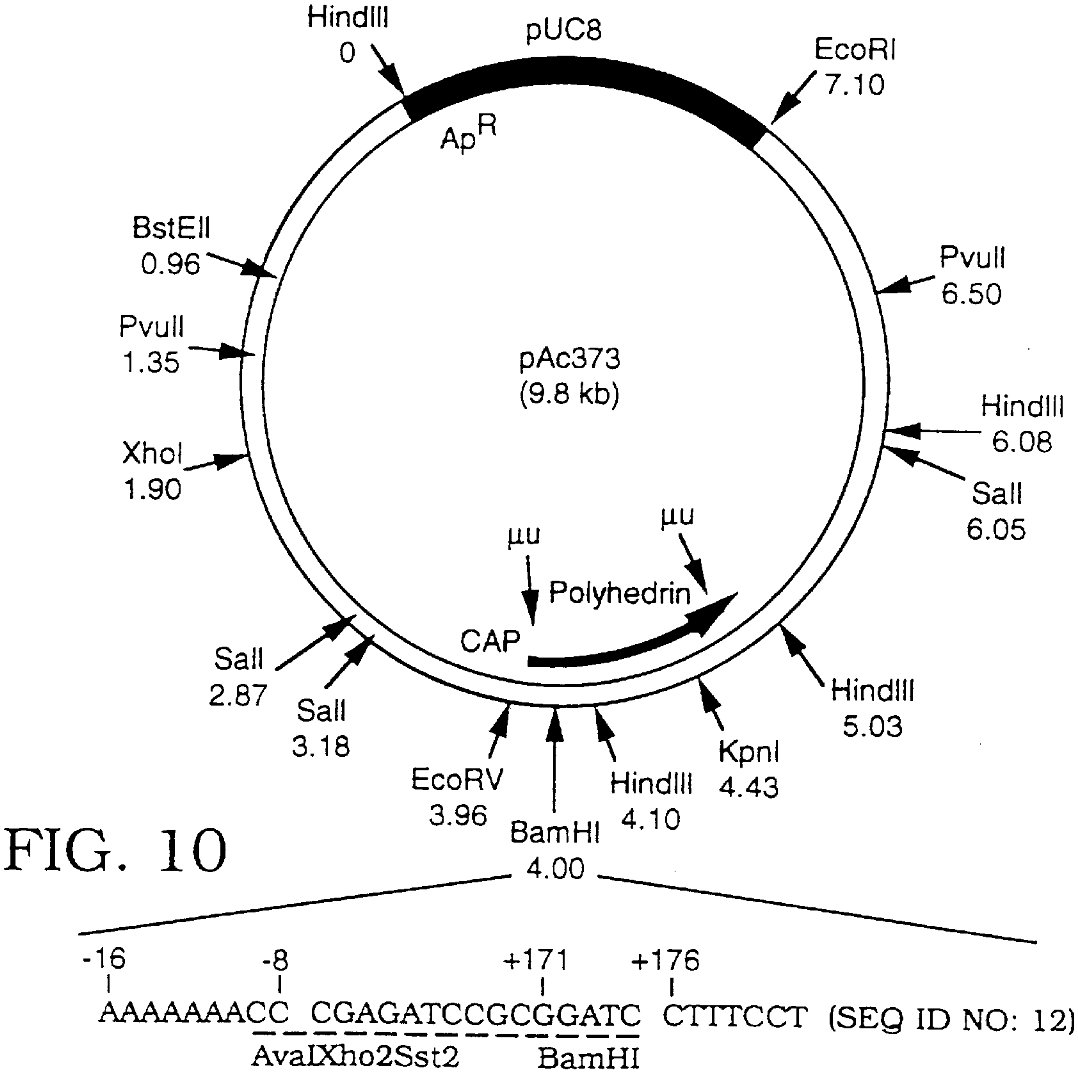

FIG. 10: A schematic drawing of pAc373.

Figure 11:
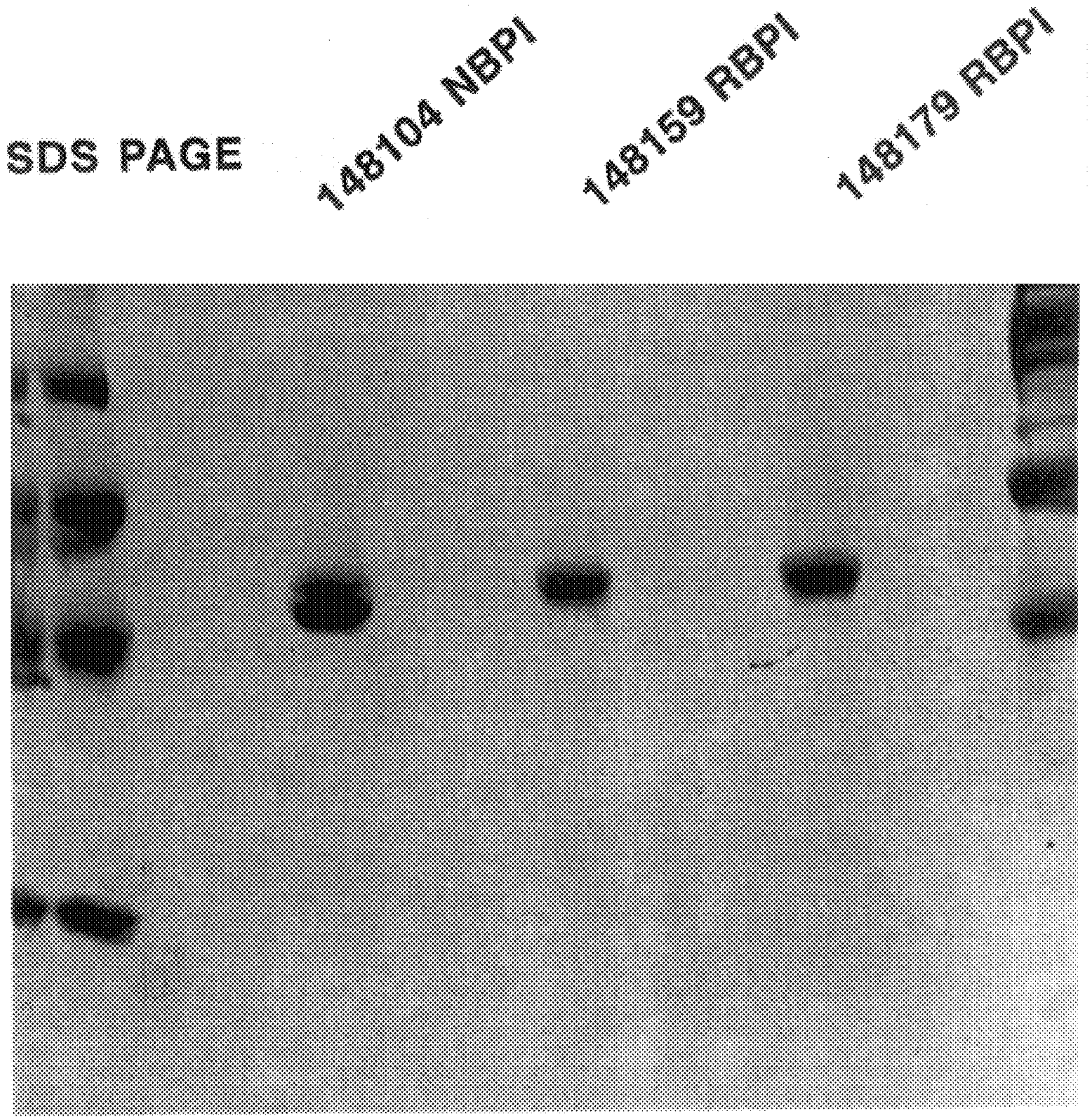

FIG. 11: SDS-PAGE analysis of (1) nBPI Protein (Lot No. #148104), (2) rBPI Protein (Lot No. #148159), and (3) rBPI Protein (Lot No. #148179).

FIGS. 12A–12D: cDNA sequence (SEQ ID NO: 14) of BPI.

FIG. 13: Protein sequence (SEQ ID NO: 15) for p337.

FIG. 14: Protein sequence (SEQ ID NO: 16) for p212.

Figure 15:
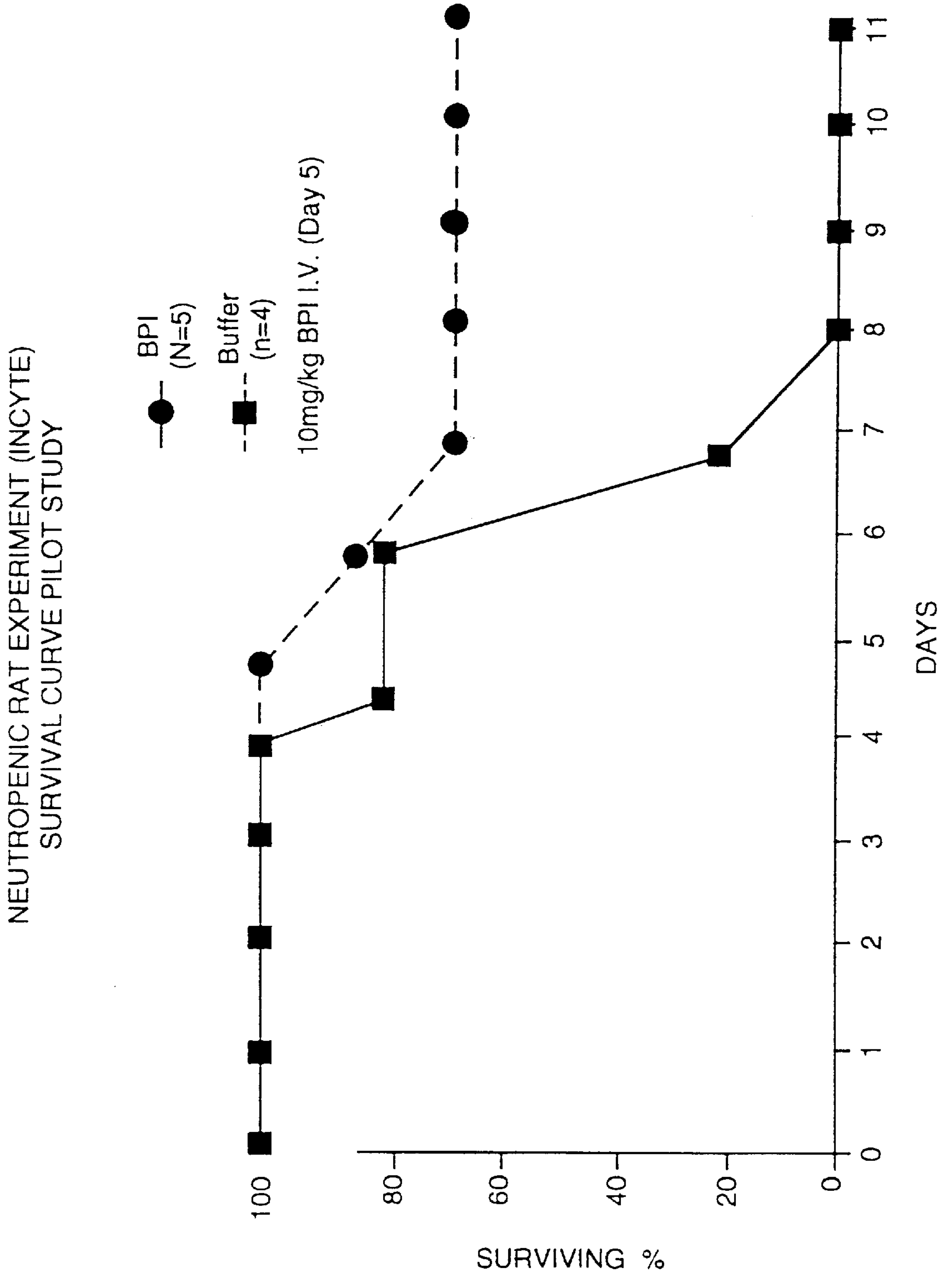

FIG. 15: Line graph showing BPI efficacy using neutropenic rat models.

Figure 16:
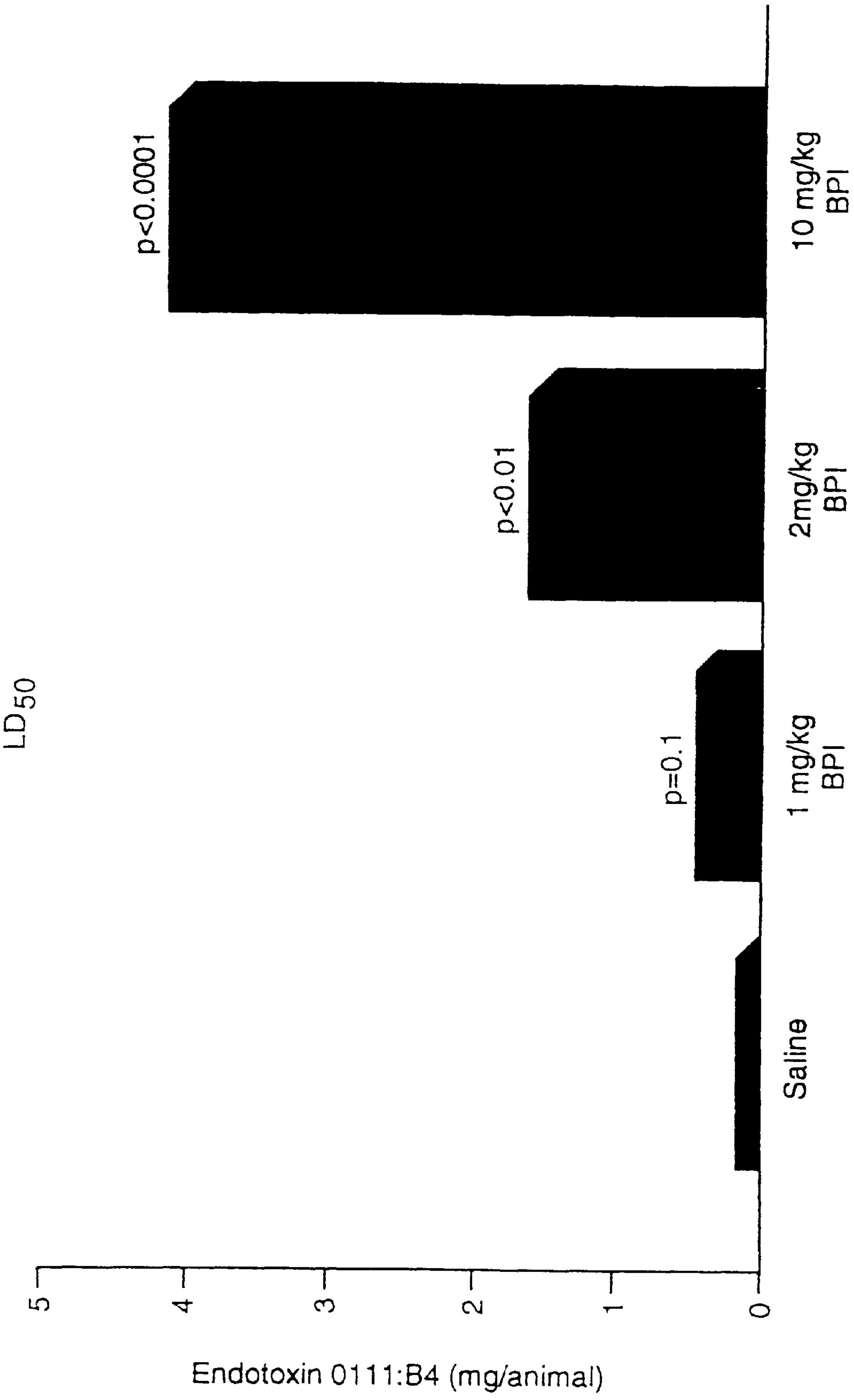

FIG. 16: Bar graph showing BPI efficacy in vivo.

Figure 17:
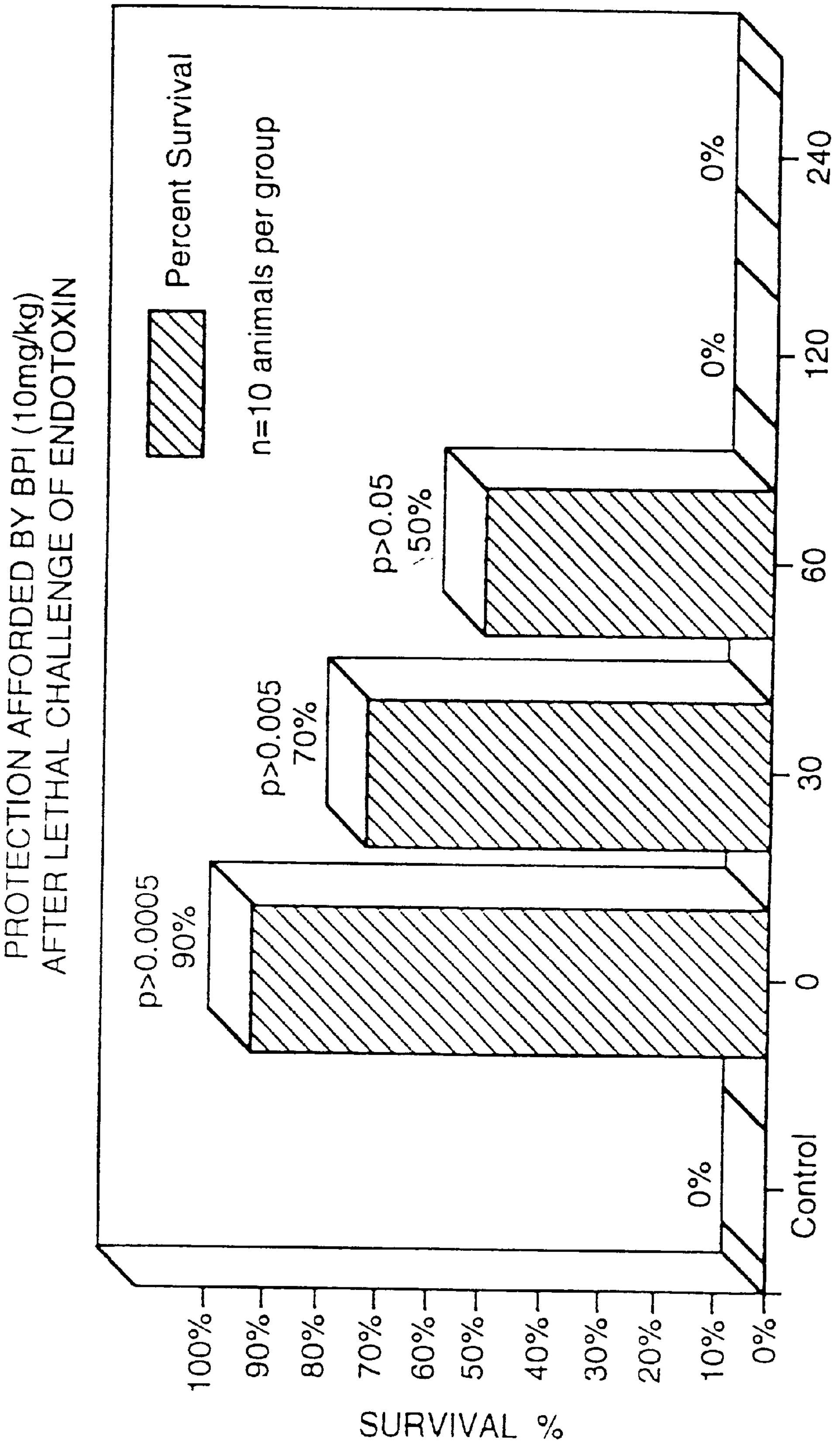

FIG. 17: Bar graph showing BPI efficacy.

Figure 18:
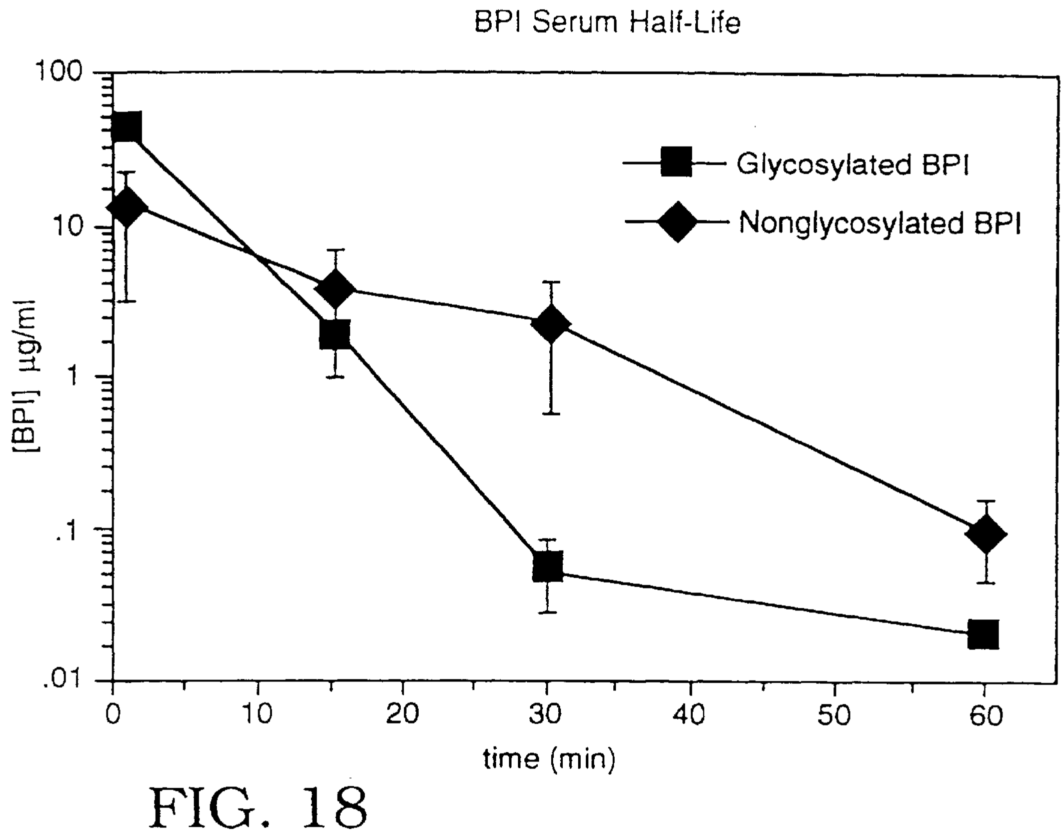

FIG. 18: Line graph showing BPI serum half life.

Figure 19:
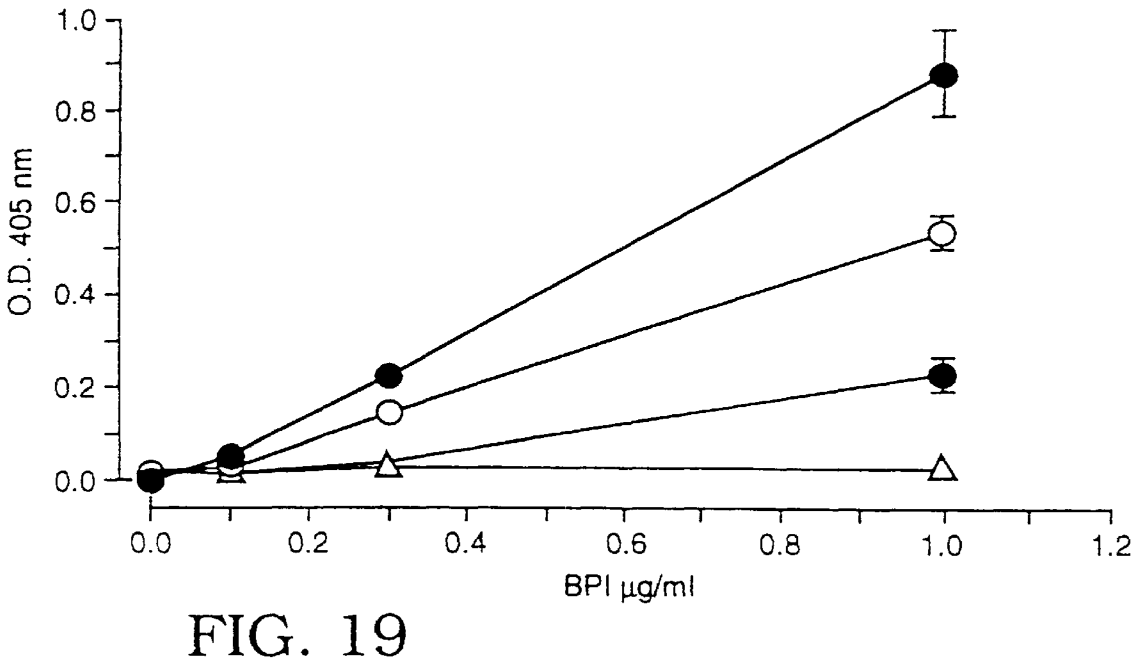

FIG. 19: Line graph showing BPI binding to endotoxin. BPI binding was assayed on endotoxin coated wells which were treated with varying concentrations of polymyxin B sulfate. Results show absorbance (O.D. 405) for buffer control (closed circles). 10 $\mu$g/ml polymyxin B (open circles). 100 $\mu$g/ml polymyxin B (closed triangles). 1 mg/ml polymyxin B (open triangles). Data is represented as the mean±SK of quadruplicate values.

Figure 20:
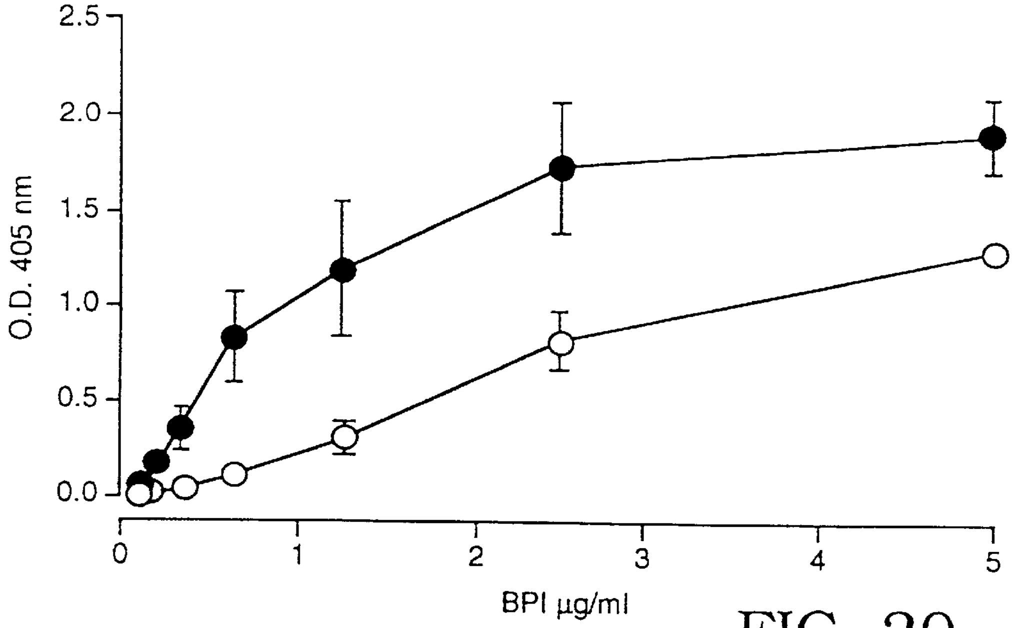

FIG. 20: Line graph showing BPI endotoxin binding. BPI was diluted in buffer (closed circles) or neat plasma (open circles) and assayed for endotoxin binding.

Figure 21:
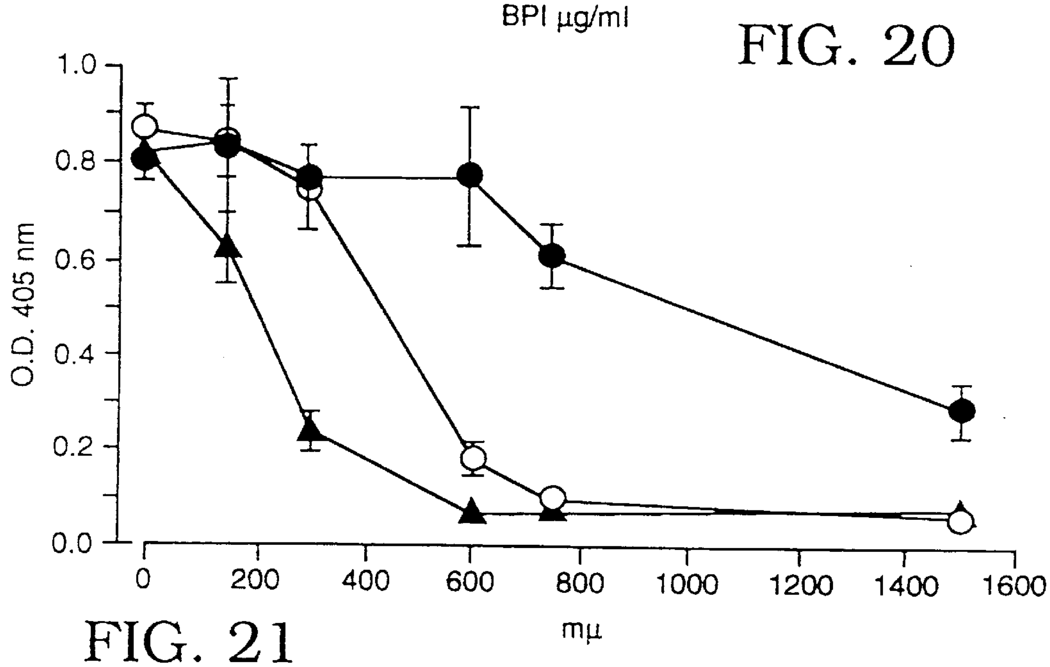

FIG. 21: Line graph showing BPI endotoxin binding. BPI was diluted in increasing concentrations (expressed as ionic strength, m$\mu$) of NaCl (closed circles), $MgCl_2$ (open circles), or $CACl_2$ (closed triangles), and assayed for endotoxin binding as described.

Figure 22:
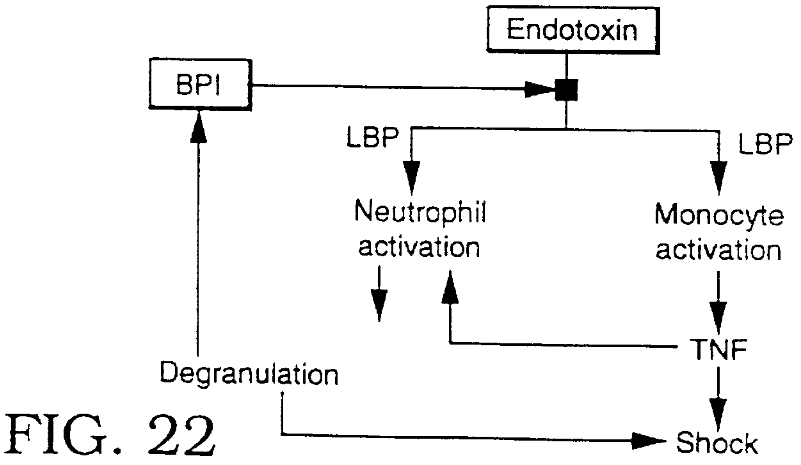

FIG. 22: A schematic diagram showing the role of BPI and LBP in regulating endotoxin activity.

FIG. 23: A biologically active variant designated LBP/BPI Chimera (SEQ ID NO: 17).

FIG. 24: A biologically active variant designated CHO-BPI (SEQ ID NO: 18).

FIG. 25: A biologically active variant designated BPI (DP linkage) (SEQ ID NO: 19).

FIG. 26: A construct (SEQ ID NO: 26) for making biologically active variants of BPI.

DETAILED DESCRIPTION OF THE INVENTION

As used in this application, the following words or phrases have the meanings specified.

As used herein, "BPI" means a native or naturally occurring biologically active human 57 kd protein which binds to the outer membrane of susceptible gram negative bacteria.

As used herein, "biologically active polypeptide fragment of BPI" means a polypeptide of molecular weight less than 57 kd, having the biological activity of, and an amino acid sequence present within, BPI.

As used herein, "biologically active polypeptide analogs of BPI" means a polypeptide which has substantially the same amino acid sequence as, and the biological activity of, BPI. Biologically active polypeptide analogs of BPI include polypeptide, the sequence of which varies from the sequence of BPI by a changed amino acid within the BPI sequence, e.g. a mutation, or by the addition of one or more amino acids at the amino- or carboxy- terminus, or both, of the BPI sequence.

As used herein, "biologically active variant of BPI" means a polypeptide that (1) includes a portion of the amino acid sequence which is present within BPI and an amino acid sequence which is not present within BPI, and (2) has substantially the same biological activity, i.e. endotoxin-neutralizing activity, as BPI.

As used herein, "recombinant" means a polypeptide produced by genetic engineering methods. Thus, each of BPI, biologically active polypeptide fragments of BPI, biologically active polypeptide analogs of BPI, and biologically active variants of BPI may be recombinant. However, in the context of this application, BPI is not the same as recombinant BPI, the latter differing in some molecular characteristic from the native or naturally occurring polypeptide, e.g. in glycosylation pattern.

As used herein, BPI Protein means (1) BPI, (2) a biologically active fragment of BPI, (3) a biologically active polypeptide analog of BPI, or (4) a biologically active variant of BPI, each of which may be either recombinant or nonrecombinant.

The present invention provides a composition comprising a BPI Protein and an anionic compound which composition exhibits (1) no bactericidal activity and (2) endotoxin neutralizing activity.

In accordance with the practice of this invention, the anionic compound could be a protein, a proteoglycan (for example heparin) or a synthetic polymer (for example dextran sulfate or polyglutamic acid). Preferably, the anionic compound is a protein such as serum albumin.

This invention also provides a biologically active variant of BPI which (1) specifically binds to endotoxin, (2) competes with BPI Protein for binding to endotoxin, and (3) inhibits endotoxin-induced lethality.

As used in this application the term "endotoxin" means a bacterial toxin which is pyrogenic.

One example of a biologically active fragment of BPI is shown in FIG. 13 (SEQ ID NO: 15). Another example of a biologically active fragment of BPI is shown in FIG. 14 (SEQ ID NO: 16).

Additionally, examples of a biologically active variant of BPI is shown in FIG. 23 (SEQ ID NO: 17). Another example of a biologically active variant of BPI is shown in FIG. 24 (SEQ ID NO: 18). Further, yet another example of a biologically active variant of BPI is shown in FIG. 25 (SEQ ID NO: 19).

The present invention further provides a method for producing and secreting a recombinant BPI Protein from a cell. This method comprises (a) constructing a vector comprising DNA encoding BPI Protein; (b) transfecting the cell with the vector; and (c) culturing the cell so transfected in culture medium under conditions such that BPI Protein is secreted. In accordance with this invention, the vector further comprises a signal sequence.

In accordance with this method, mammalian cells are preferred. Examples of a mammalian cell includes, but is not limited to, HeLa, CHO, DUX B11, Sp2/0, W138, DHK, HEPG2, and COS-1 cells.

This invention also provides a BPI Protein produced by the above-described method. In one embodiment the BPI Protein is a recombinant BPI Protein designated 148159 rBPI protein shown in FIG. 11. Additionally, the invention provides a recombinant BPI protein designated as 148179 rBPI protein shown in FIG. 11.

Interestingly, recombinant BPI Protein produced in mammalian cells such as Chinese hamster ovary (CHO) cells exhibit a slightly altered migration pattern on sodium dodecyl sulfate polyacrylamide gel electrophoresis (SDS-PAGE)

indicating that the molecule may also be processed differently in mammalian cells than in neutrophils or HL60 cells. Such processing may be either responsible for, or a result of, the molecule being secreted rather than packaged into granule membranes.

This invention also provides a glycosylated BPI Protein.

In accordance with the above described method, the BPI Protein so secreted may be a full length soluble BPI Protein.

Also, the present invention provides a method for producing a recombinant BPI Protein from a bacterial cell. This method comprises (a) constructing a vector without a signal sequence and comprising DNA encoding BPI Protein; (b) transfecting the bacterial cell with the vector; and (c) culturing the bacterial cell so transfected in culture medium under conditions such that recombinant BPI Protein is produced. An example of a bacterial cell includes but is not limited to *E. coli.*

BPI Protein has been shown to be toxic to bacteria, however, the toxic effects of the BPI Protein so produced against bacteria may be overcome by deleting the normal leader sequence in the vector comprising the BPI protein cDNA.

Apparently, when the signal sequence is included in the expression plasmid as provided in a full length clone and reported by Gray et al. ((1989) Journ. of Biol. Chem., 264:9505) no bacterial colonies are obtained, whereas, numerous colonies can be obtained if the signal sequence is deleted. Further, the method described hereinabove provides for expression of full length BPI Protein in a nonglycosylated form. The invention further provides for a nonglycosylated form of BPI Protein which is free from glycosylated BPI Protein.

The subject invention further provides a method for producing a recombinant BPI Protein from an insect cell. This method comprises (a) constructing a vector without a signal sequence and comprising DNA encoding BPI Protein; (b) transfecting the insect cell with the vector; and (c) culturing the insect cell so transfected in culture medium under conditions such that BPI Protein is secreted.

In one example of the above-described method, insect cells function as hosts for a baculovirus vector containing a sequence encoding the BPI Protein. Also, BPI protein derived from insect cells exhibit a different migration pattern on SDS-PAGE than that derived from either mammalian cells or the BPI protein found naturally-occurring in neutrophils. Thus, the invention provides for a new molecular species of BPI Protein as processed by baculovirus infected insect cells.

Further, this invention provides a biologically active variant of BPI produced by the above-described method.

Also, this invention provides a method for determining the amount of endotoxin in a sample from a subject which comprises contacting the sample with a BPI Protein under conditions such that an endotoxin-BPI Protein complex is formed, detecting the amount of the complex so formed thereby determining the amount of endotoxin in the sample.

Additionally, the present invention provides a method for determining the amount of endotoxin in a sample containing bound and unbound endotoxin from a subject. This method comprises (a) treating the sample so as to denature any endotoxin binding protein to which the endotoxin may be bound thereby obtaining unbound endotoxin; (b) contacting the treated sample with a BPI Protein under conditions such that the BPI Protein binds to unbound endotoxin of step (a) so that a endotoxin-BPI Protein complex is formed; (c) detecting the amount of the complex so formed thereby determining the amount of endotoxin in the sample.

In accordance with the invention, denaturation in step (a) may be effected using an elevated temperature. For example, the elevated temperature may be 95 degrees centigrade. Alternatively, denaturation may be effected with an acid.

This present invention also provides a method of detecting endotoxin in a sample which comprises contacting the sample with a BPI Protein such that the endotoxin binds to the BPI Protein and forms a complex therewith; and detecting such complex.

In one example of the invention, the sample containing endotoxin is transferred onto a suitable support under conditions permitting endotoxin in the sample to attach to the support prior to contacting the sample with BPI Protein labeled with a detectable moiety.

This invention further provides a method for diagnosing endotoxemia in a subject which comprises obtaining from the subject a biological fluid sample, detecting endotoxin in such sample using the above-described method and thereby diagnosing such disorder. The sample may be a cellular sample. Alternatively, the sample may be a biological fluid sample such as serum, urine, blood, a tissue extract, or sputum.

In accordance with the practice of the invention, the BPI Protein may be labeled with a fluorescent label and detection may be effected by a fluorometer. Alternatively, the BPI Protein may be labeled with a radioactive label and detection may be effected by a radiograph. Further, the BPI Protein may be labeled with an enzyme and detection may be effected by a spectrophotometer.

The present invention further provides a method for coating a surgical tool with a BPI Protein so that the BPI Protein will complex with endotoxin which method comprises attaching BPI Protein onto a surface of the tool which surface is designed for contact with a biological sample.

Also, this invention provides a method for coating an implantable, invasive device with a BPI Protein so that it will form a complex with endotoxin which method comprises attaching BPI Protein onto a surface of the device which surface is designed for contact with a biological sample.

In accordance with the practice of the present invention, the biological sample may be blood. Alternatively, the biological sample may be a tissue sample. Further, the biological sample may be a muscle sample. Also, the biological sample may be cartilage. Additionally, the biological sample may be bone.

Also, in accordance with the practice of this invention, the surgical tool may be a catheter tubing.

Alternatively, the surgical tool may be a surgical staple.

Further, in accordance with the practice of this invention, the device may be a surgical implant.

The present invention further provides a method for decontaminating a fluid containing endotoxin prior to administration of the fluid into a subject which comprises contacting the fluid with BPI Protein prior to administration, under conditions such that endotoxin forms a complex with BPI Protein, thereby decontaminating the fluid. The fluid may be blood, plasma, blood serum, an isotonic solution, a pharmaceutical agent, a cell culture reagent, or bone marrow.

This invention also provides a kit for detecting the presence of BPI Protein in a biological fluid sample which comprises (a) polymyxin B in an assay buffer which binds unbound endotoxin molecules; (b) a first antibody attached to a surface area containing the assay buffer, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody an active BPI Protein contained in the biological fluid sample is bound by the first and second antibody thus forming a first antibody-BPI Protein-second antibody complex, detecting such complex, and thereby detecting BPI Protein in the biological fluid sample.

Also, this invention provides a kit for determining the amount of BPI Protein in a biological fluid sample which comprises (a) polymyxin B in an assay buffer which binds unbound endotoxin molecules; (b) a first antibody attached to a surface area containing the assay buffer, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody an active BPI Protein contained in the biological fluid sample is bound by the first and second antibody thus forming a first antibody-active BPI Protein-second antibody complex, detecting such complex, and determining the amount of active BPI Protein in the biological fluid sample.

Additionally, this invention provides a method for preventing endotoxemia in a subject which comprises administering to the subject an amount of a BPI Protein effective to bind to endotoxin so as to prevent endotoxemia in the subject.

The present invention provides a method for treating a subject suffering from endotoxemia which comprises administering to the subject an amount of a BPI Protein effective to bind endotoxin so as to treat the subject suffering from endotoxemia.

In accordance with the practice of the invention, the effective amount of the BPI Protein for preventing endotoxemia or treating a subject suffering from endotoxemia may be between about 0.1 and about 10 mg/kg body weight of subject. Also, the effective amount may be an amount between about 1 and about 10 mg/kg body weight of subject.

This invention is illustrated in the Experimental Details section which follows. This section is set forth to aid an understand of the invention but is not intended to, and should not be construed to, limit in any way the invention as set forth in the claims which follow.

EXPERIMENTAL DETAILS

EXAMPLE 1

Materials and Methods

Reagents and Solutions

Endotoxin from *E. coli* 0111:B4 and from *S. typhimurium* RE mutant were purchased from RIBI Immunochem Research, Inc., Hamilton, Mont. FMLP, cytochalasin B and polymyxin B sulfate (7900 U/mg) was purchased from Sigma Chemical Co., St. Louis, Mo. Natural human tumor necrosis factor was purchased from Endogen Inc., Boston Mass. HBSS without calcium and magnesium and RPMI 1640 were purchased from Gibco BRL, Grand Island, N.Y.

BPI Purification

BPI was purified from neutrophil granule preparations as previously described (Marra, M. N. et al. J. Immunol. 144: 662, 1990) with the exception that the purification was performed under rigorously pyrogen-free conditions using new, pyrogen-free columns and de-pyrogenated buffers. Buffers were deyprogenated using a Pyrosart filter (Sartorius Filters, Hayward, Calif.). Purification of BPI under these conditions resulted in material with approximately four-fold greater activity for neutralizing endotoxin-mediated neutrophil stimulation than previously reported (Marra, M. N. et al. J. Immunol. 144: 662, 1990).

Immunoaffinity purification of anti-BPI antibodies

Sera was collected from rabbits immunized with a 20 amino acid peptide corresponding to the N-Terminal 20 amino acids of the BPI molecule (BPI peptide 1-20). The IgG fraction of pooled sera was purified using Protein A Sepharose (Pharmacia, Piscataway, N.J.). Specific anti-peptide IgG was purified from this fraction using BPI peptide 1-20 coupled to activated CNBr Sepharose (Pharmacia). Bound IgG was collected and pooled, and the adsorbed IgG was further depleted of residual specific antibody by passing over the peptide column three additional times to generate immunoadsorbed negative control. Antibody concentration was determined by optical density at 280 nm. Immunoaffinity purified and adsorbed IgG were tested for specificity by Western blotting. No activity was observed in the immunoadsorbed control IgG, even at concentrations $10^3$-fold greater than that utilized for the immunoaffinity purified antibody.

Endotoxin Binding Assay

BPI binding to endotoxin immobilized on microtiter plates was performed using a modified procedure described by Tobias, P. S. et al. J. Biol. Chem. 264:10867, 1989. Briefly, Immulon 2 96 well microtiter plates (Dynatech Biotechnology Products, Chantilly, Va.) were coated with 4 μg/well glycolipid from *Salmonella typhimurium* RE mutant in 50 mM borate pH 9+20 mM EDTA overnight at 37° C. Plates were then washed extensively under running distilled deionized water, then dried at 37° C. Assay plates were blocked for 30 minutes at 37° C. with smg/ml very low endotoxin BSA (Sigma, St. Louis, Mo.) prepared in pyrogen-free PBS. Plates were flicked, and in some experiments polymyxin B was added to the wells and incubated for an additional 30 minutes at 37° C. Plates were flicked again, and BPI samples were added. All buffers containing BPI or polymyxin B were prepared in pyrogen-free PBS. BPI samples diluted in pyrogen free buffer, or in some experiments, serum or plasma from normal human volunteers, were incubated for 3 hours at 37° C. with shaking. The plates were washed with PBS containing 1 mg/ml pyrogen free BSA, then developed, using rabbit polyclonal anti-BPI peptide lgG antibody as described followed by goat-anti-rabbit IgG-alkaline phosphatase conjugate (Gibco BRL Life Technologies, Inc., Grand Island, N.Y.). Absorbances were read at 405 nm on a Vmax kinetic microplate reader (Molecular Devices Inc., Menlo Park, Calif.).

BPI inhibition of endotoxin mediated TNF induction by human adherent mononuclear cells Blood collected in acid citrate dextrose containing vacutainer tubes (Becton Dickinson, Rutherford, N.J.) was diluted in Hank's balanced salt solution (HBSS) minus $Ca^2$+ and $Mg^{2+}$. Mononuclear cells were separated using Ficol-Paque (Pharmacia Inc., Piscataway, N.J.), collected and washed three time in HBSS, and the proportion of monocytes was estimated by microscopic examination. Cells were brought up to an appropriate volume of RPMI 1640 with glutamine and antibiotics and without serum to give approximately $1\times10^6$ monocytes/ml. Cells were plated into 96 well flat bottom tissue culture plates (Costar, Cambridge, Mass.), 200 μl/well, and incubated for 2 hours at 37° C. in a humidified incubator with 7% $O_2$. Cells were then washed three times in warm RPMI 1640 without serum. After the last wash was aspirated, 200 μl/well RPMI 1640 with 10% autologous heat inactivated serum was added. To each well was then added the 22 μl of 10× solution of *E. coli* Endotoxin preincubated in buffer, polymyxin B, or BPI. Cells were incubated with the endotoxin mixture for 4 hours at 37° C., then the supernatants were collected and assayed for TNFα antigen by ELISA (Endogen Inc., Boston, Mass.).

Inhibition of endotoxin-induced TNFα secretion by murine broncheoalveolar macrophages Normal anesthetized Swiss-Webester mice were challenged by the intranasal route with 10 ng *E. coli* 0111:B4 endotoxin (List, Campbell, Calif.). Twenty minutes before challenge, anesthetized mice were treated by the intranasal route with 50 μl saline, BPI or polymyxin B solution. At one hour after endotoxin challenge, mice were re-anesthetized, and 0.7 ml of saline containing 1% human serum albumin was added to the lungs via the trachea. The lungs were gently kneaded. A 0.5 ml volume bronchoalveolar lavage (BAL) fluid was aspirated, cells were pelleted by centrifugation, and the BAL sample was stored at −70° C. The TNFα level in the BAL fluid was determined by measuring cytotoxicity towards WEHI clone 13 mouse fibrosarcoma cells. Human rTNFα (Chiron, Emeryville, Calif.) was used as the standard.

RESULTS

BPI binds to bacterial lipopolysaccharide

Binding of BPI to endotoxin was demonstrated using a modified ELISA protocol to detect BPI bound to immobilized *S. typhimurium* Re endotoxin as described in Methods above. BPI had bound endotoxin in a concentration dependent manner and binding was inhibited by polymyxin B/suggesting that BPI binds at or near lipid A (FIG. 19). significant binding of BPI to endotoxin was retained in the presence of plasma (FIG. 20) or serum, thus indicating that BPI binds to endotoxin in the presence of blood proteins as well as physiologic salts. This date is consistent with the observation by Mannion, B. A. et al. (J. Clin, Invest. 86:631 1990) that BPI binds to bacteria in the presence of serum albumin, although under these conditions BPI is not bactericidal. Also, concentrations of $Ca^{2+}$ and $Mg^{2+}$ which can rescue bacteria from the lethal actions of BPI (20–80 mM) do not significantly reduce binding of BPI to endotoxin (FIG. 21).

BPI blocks endotoxin-mediated TNF secretion in vitro

Release in TNF in response to endotoxin in vivo may play an important role in pathogenesis of endotoxic shock. To investigate the role of BPI in regulating endotoxin-mediated TNF secretion, we measured TNF secretion by human adherent peripheral blood mononuclear cells in response to endotoxin and to endotoxin preincubated with BPI (Table 1). BPI specifically prevented endotoxin-stimulated TNF secretion by these cells in a concentration dependent manner. In addition, inhibition by BPI could be overcome by a large excess of endotoxin (100–1000 ng/ml) or 0.1% killed *S. aureus,* indicating that BPI did not interfere with monocyte function but rather blocked specific activation of monocytes by endotoxin.

TABLE 1

Inhibition of endotoxin-Induced TNF Production by BPI

| Endotoxin ng/ml | TNF (pg/ml) Buffer Control | Polymyxin 1.0 μg/ml | BPI 0.4 μg/ml | BPI 0.1 μg/ml |
|---|---|---|---|---|
| 100 | 823 ± 67 | 400 ± 148 | 530 ± 16 | 746 ± 48 |
| 10 | 756 ± 116 | 76 ± 25 | 60 ± 9 | 182 ± 42 |
| 1 | 598 ± 89 | 0 | 0 | 0 |

Human peripheral blood mononuclear cells were stimulated with *E. coli,* 0111:B4 endotoxin which had been preincubated for 30 minutes at 37° C. with buffer, BPI or polymyxin B. Supernatants were harvested four hours after endotoxin mixtures were added. Secretion of TNFA was quantitated by ELISA.

BPI blocks in vivo pyrognicity of endotoxin

Cytokines released in response to experimental endotoxin infusion cause physiologic changes including fever induction. We studied the effects of BPI on endotoxin pyrogenicity by injecting rabbits with endotoxin or endotoxin preincubated with BPI. Resulting changes in temperature were monitored at three one-hour intervals post injection. The greatest temperature increase was used to calculate $\Sigma(\Delta T)$ for the three animals test in each group. A value of ≧1.4° C. is considered pyrogenic (U.S. Pharmacopeal Convention, Inc. 1990 Rockville, Md., Test 151, p. 1515). While a total Temperature rise of 3.9° C. was observed in the group injected with 400EU of FDA reference standard endotoxin alone, endotoxin pre-treated with 2 μg BPI was not pyrogenic, showing a total temperature rise of only 1.1° C. No response was observed in buffer treated control animals or BPI treated animals.

BPI blocks endotoxin-mediated TNPF secretion in vivo

To determine whether BPI could inhibit endotoxin-mediated TNFα secretion in vivo, we tested BPI neutralization of endotoxin in the murine lung. Administration of BPI into the lung twenty minutes prior to endotoxin challenge significantly reduced the amount of TNF secreted into bronchoalveolar lavage fluid by alveolar macrophages (Table 2). Four out of five saline treated mice had TNFα levels greater than 1,000 pg/ml, versus one of five for BPI. Overall, BPI reduces endotoxin-mediated TNFα secretion by murine lung alveolar macrophages by 8.2-fold. Relative to the saline control, reduction of TNF secretion by BPI was significant (using the Student's t-test) at the $p<0.05$ level. (Geometric mean±SD of saline control: 3.364±0.402, BPI treated group=2.109±0.764). Polymyxin B was slightly more effective in reducing THFα secretion relative to the saline control ($p<0.02$) although the dose of PMB was 50-fold greater on a molar basis than that used for BPI. These data indicate the soluble BPI neutralizes endotoxin in vivo.

TABLE 2

Effect of BPI on endotoxin-Mediated TNF Secretion by Murine BAL

| Mouse | TNF (pg/ml) Saline Control | BPI 0.86 μg (15 pmol) | Polymyxin B 1.0 μg (782 pmol) |
|---|---|---|---|
| 1 | 1200 | 15 | 74 |
| 2 | 675 | 63 | 50 |
| 3 | 5560 | 425 | 132 |

TABLE 2-continued

| Effect of BPI on endotoxin-Mediated TNF Secretion by Murine BAL TNF (pg/ml) | | | |
|---|---|---|---|
| Mouse | Saline Control | BPI 0.86 μg (15 pmol) | Polymyxin B 1.0 μg (782 pmol) |
| 4 | 2800 | 67 | 370 |
| 5 | 5250 | 1310 | 640 |
| Mean ± SD | 3097 ± 2250 | 376 ± 547 | 253 ± 251 |

Normal anesthetized mice were challenged by the intranasal route with 10 ng *E. coli* 0111:B4 endotoxin. Twenty minutes before challenge, anesthetized mice were treated by the intranasal route with 50 μl saline, BPI or polymyxin B solution. Bronchoalveolar lavage (BAL) fluid was assayed for TNFα by measuring cytotoxicity towards WEHI as clone 13 mouse fibrosarcoma cells. Human rTNFα was used at the standard.

Our data show that BPI specifically prevented endotoxin-stimulated TNF secretion in vitro by human adherent mononuclear cells in a concentration dependent manner. Inhibition of endotoxin-induced TNF secretion distinguishes BPI from LBP. LBP, a 60 kDa acute phase protein synthesized by hepatocytes, has 44% amino acid sequence homology to BPI and binds to endotoxin in vivo and in vitro (Tobias, P. S., K. Soldau, and R. J. Ulevitch. 1986. Isolation of a lipopolysaccharide-binding acute phase reactart from rabbit serum. J. Exp. Med. 164:777) (Schuman, R. R., S. R. Leong, G. W. Flaggs, P. W. Gray, S. D. Wright, J. C. Mathison, P. S. Tobias, and R. J. Ulevitch. 1990. Structure and function of lipopolysacchride binding protein. Science. 248:1429). Despite their structural similarities, BPI and LBP are functionally antagonistic. LBP-endotoxin complexes prime neutrophils for the oxidative burst response to FMLP and cause accelerated and increased TNF production by monocytes in vitro (Vosbeeck, K., L. Sklar, H. Muller, C. Lundberg, C. Hanson, K. Arfors, R. Ulevitch, and P. Tobias. 1988. Modulation of lipopolysaccharide (LPS) induced neutrophil priming by an acute phase reactant, lipopolysaccharide binding protein, LBP. Eur. J. Clin Invest. 18A50) (Wright. S. D., R. A. Ramos, P. S. Tobias, R. J. Ulevitch, and J. C. Mathison. CD14, a receptor for complexes of lipopolysaccharide (LPS) and LPS binding protein. Science. 249:1931) (Tobias, P. S., J. C., Mathison, and R. J. Ulevitch. 1988. A family of lipopolysaccharide binding proteins involved in responses to Gram-negative sepsis. J. Biol. Chem. 263:13479) In contrast, BPI blocks LPS-mediated stimulation of both neutrophils (Marra, M. N., C. G. Wilde, J. E. Griffith, J. L. Snable and R. W. Scott. 1990. Bactericidal/permeability increasing protein has endotoxin-neutralizing activity. J. Immunol. 144:662) and macrophages in vitro. Since BPI-endotoxin complexes fail to stimulate inflammatory cells in vitro, one would not expect such complexes to elicit a pyrogenic response when administered in vivo. Small quantities of endotoxin alone induce a strong pyrogenic response resulting from the release of endogenous pyrogens such as TNF, IL-1, and gamma IFN (Farley, M. M., W. M. Shafer, and J. K. Spitznagel. 1988. Lipopolysaccharide structure determines ionic and hydrophobic binding of a cationic antimicrobial neutrophil granule protein. Infect. Immun. 56:1589). Rabbits are exquisitely sensitive to trace quantities of endotoxin, and respond with a dose dependent and reproducible elevation of core temperature. In complex with BPI, endotoxin was unable to stimulate a pyrogenic response in rabbits. Thus, BPI is an effective inhibitor of endotoxin in vivo presumably a result of BPI blocking endotoxin-mediated cytokine secretion.

The bactericidal and permeability increasing activities of BPI in vitro are associated with the N-terminal half of the molecule which shares extensive homology with LBP (Schuman, R. R., S. R. Leong, G. W. Flaggs, P. W. Gray, S. D. Wright, J. C. Mathison P. S. Tobias, and R. J. Ulevitch. 1990. Structure and function of lipopolysaccharide binding protein. Science. 249:1429). No function has been ascribed to the carboxy-terminal region, other than a membrane spanning domain. Gray and colleagues (Gray, P. W., G. Flaggs, S. R. Leong, R. J. Gumina, J. Weiss, C. E. Ooi, and P. Elsbach. 1989. Cloning of the cDNA of a human neutrophil bactericidal protein. Structural and functional correlations. J. Biol. Chem. 264:9505) suggest that the carboxy-terminal half of BPI is associated with the azurophil granule membrane. In their model, when neutrophils are stimulated, proteolytic enzymes such as elastase cleave the molecule releasing the active, bactericidal N-terminal half into the phagolysosome. Several lines of evidence, however, argue against BPI as an integral membrane protein. BPI can be extracted from isolated azurophil granules in the absence of detergents. BPI is soluble in aqueous solutions and soluble BPI is active in tests for both endotoxin binding and inhibition. Also, BPI is released by FMLP/cytochalasin B stimulated neutrophils (71% of total cellular BPI) as a full-length, protein, arguing against release of the N-terminus by neutrophil proteases upon degranulation.

In vivo, BPI likely functions to suppress endotoxin toxicity and not as a bactericidal protein. Endotoxin binding proteins such as LBP and BPI may function respectively as a receptor/receptor-antagonist system to regulate the host response to endotoxin (FIG. 22). LBP acts as a soluble receptor for endotoxin and amplifies the effects of endotoxin on both neutrophils and macrophages. The ability of BPI to limit the host response to endotoxin indicates that BPI may have an important role in blocking lethal effects of endotoxin in vivo. Preliminary results in animals (see Example 4) show that treatment with recombinant BPI markedly reduces endotoxin-induced lethality. Thus, use of BPI to neutralize endotoxin, in conjunction with conventional antibiotics to limit bacterial growth, may be a useful therapy against endotoxic shock.

EXAMPLE 2

Expression of BPI Proteins and BPI-Truncated Forms

A. Genetically Engineered Mammalian Cells Express BPI

In order to produce BPI protein and/or BPI protein variants in mammalian cells, the cDNA sequences must be inserted into a suitable plasmid vector. A suitable vector for such an application is pSV-1, which contains the origin of replication and early and late promoters of SV40, followed by multiple insert cloning sites, followed by the termination sequences from the hepatitis B surface antigen gene. Also contained within the plasmid are an origin of bacterial DNA replication, and the genes encoding ampicillin resistance and dihydrofolate reductase. Similar vectors have been used to express other foreign genes (McGrogan, et.al. Biotechnology 6, 172–177). Vector DNA was prepared for acceptance of BPI protein CDNA sequences by digestion with HindIII and Bam HI, and dephosphorylation with alkaline phosphatase.

Several BPI protein cDNA-containing inserts were prepared for insertion into pSV-1. First, an insert encoding full-length BPI protein was prepared by digestion of the parent plasmid with appropriate restriction enzymes for ex. EcoRI and Bgl II, yielding two DNA fragments containing portions of the BPI protein coding sequence. These two fragments were ligated together into prepared SV-1, and the recombinant clones obtained were screened by restriction enzyme digestion for the presence of the two inserts in the proper orientation. Two cDNAs encoding truncated forms of BPI protein were generated using oligonucleotide-directed DNA amplification of the parent BPI protein insert DNA. The amplifying oligos were designed to replace codons 212 (oligo 459) (SEQ ID NO: 4) (FIG. 6) and 337 (oligo 460) (SEQ ID NO: 8) (FIG. 7) with stop codons, in addition to a BamHI cloning site (FIG. 5). At the 5'-end of both constructs, oligo 458 (SEQ ID NO: 11) was used in the amplifications to create a HindIII site immediately upstream of the translational start codon ATG (FIG. 8). Thus, three BPI-encoding inserts were created, each encoding 55 kDa, 38 kDa, and 25 kDa forms of BPI, and each was ligated separately into prepared vector DNA.

Each of the three constructs was verified by restriction digest analysis, and then prepared in amounts sufficient for transfection into CHO cell line DUXB11 cells. Transfection was performed using lipofectin, and the resulting transformed cells were selected in the presence of increasing amounts of methotrexate using standard protocols.

Supernatants from either transfected pools or clones derived from the pools were assayed for the presence of endotoxin binding activity by inhibition of TNF release. BPI was negligible in the vast majority of the selected cell lines. We found that only cell lines established from a 500 nM methotrexate bulk amplification produced commercially reasonable quantities of BPI. Two such cell lines are designated 3A1 and 4D6. It was unexpected that only the bulk amplification resulted in such cell lines.

B. Baculovirus Expression of rBPI in Insect Cells

Construction of plasmid expression vector

In order to produce BPI protein and/or BPI protein variants in insect cells, the cDNA sequence must first be inserted into a suitable plasmid expression vector, such as pAC373 (FIG. 10). Appropriate restriction sites for this insertion were created by standard site-directed mutagenesis procedures. The essential properties of a suitable expression vector include a transcriptional promoter such as the polyhedron gene promoter of pAC373, and flanking homologous sequences to direct recombination into the baculovirus genome. A polyadenylation signal, such as the one from the polyhedron gene present in this plasmid vector, may or may not be necessary for expression of the recombinant gene. A marker gene such as the beta-galactosidase gene of *E. coli,* juxtaposed to regulatory sequences including a transcriptional promoter and possibly a polyadenylation signal, may be included in the vector but is not essential for BPI protein expression. A typical vector for such purposes pAC373, is shown in FIG. 10.

Creation of recombinant baculavirus

A chimeric baculovirus was created by homologous recombination between the expression plasmid containing the BPI protein target gene (or truncations thereof derived as described in Section A) and wild type baculovirus DNA. Plasmid and wild type baculovirus DNA were co-precipitated by the calcium phosphate technique and added to uninfected Spodoptera frugiperda (Sf9) insect cells. Four to seven days following transfection, cells exhibited a cytopathic morphology and contained the nuclear occlusion bodies typically produced by viral infection. The cell-free culture media containing both wild type and recombinant virus was harvested and assayed for BPI activity.

Identification and isolation of chimeric baculavirus

Clonal isolates of virus was obtained from this co-transfection stock by plaque purification on Sf9 cell monolayers overlaid with agarose. Candidate plaques for analysis will be identified by a plaque morphology negative for occlusion bodies. If the expression plasmid contains a marker gene such as beta galactosidase, recombinant plaques will be indicated by the blue color produced from a chromogenic substrate such as 5-bromo-4-chloryl-3-indolyl-β-D-galactopyranoside (X-gal) in the agarose plating medium. Picked plaques will be used for inoculation of cells in multiwell dishes. The resulting cell lysates and infected cell supernatants can be evaluated for expression of recombinant BPI, using standard activity or immunological assays. Positive wells may require additional rounds of plaque purification to obtain pure recombinant virus stocks free from wild type contamination.

Batch production of BPI

Sf9 cells are adapted to growth in serum-free, low protein medium such as ExCell (J. R. Scientific). Cells are collected from suspension culture by gentle centrifugation and resuspended in fresh medium containing the viral inoculum at a concentration of ten million cells per ml, using a multiplicity of infection of one virus plaque forming unit per cell. After a period of two hours, the culture is diluted five fold with fresh medium and incubated two to three days. At the end of that time, the cells were pelleted by centrifugation and the conditioned medium was harvested. BPI protein was purified from the cell-free supernatant by standard means.

Characterization of insect cell derived BPI

BPI protein produced in insect cells using a baculovirus expression system is a glycosylated protein of approximate molecular weight of 55,000 kd. The N-terminal amino acid sequence is identical to that of mature mammalian cell BPI, indicating correct processing of the signal sequence. The specific activity of endotoxin binding of recombinant protein was indistinguishable from BPI.

Construction of pT7BPl protein Plasmids

Oligonucleotides were prepared on an Applied Biosystems 380B DNA Synthesizer for use in oligonucleotide directed DNA amplification. The oligonucleotides created Nde I and BamHI restriction sites at the 5' and 3' ends, respectively, of the BPI protein DNA. In addition, another oligonucleotide containing a BamHI restriction site was used to create the truncated proline-212 version of the BPI protein DNA.

Following the amplification reactions, fragments were purified and digested with Nde I and BamHI. The plasmid, pGEMEX-1, (available from Promega) was selected as the vector for the constructions. pGEMEX-1 contains a T7 promoter which can be used for the expression of downstream sequences when placed into the proper host. The vector was cleaved with BamHI and, following purification, partially digested with Nde I to generate a vector with a single Nde I site and a single BamHI site. The fragments were ligated and transformed into the *E. coli* strain JM101 using the Hanahan transformation protocol (DNA Cloning Volume I, A Practical Approach, Edited by D. M. Glover, IRL Press). The transformed bacteria were plated on LB plates containing carbamicillin and incubated overnight at 37° C. Resistant colonies were selected and analyzed by preparing mini-plasmid preparations and digesting with the appropriate restriction enzymes. Digests were analyzed on both 1% agarose gels and 5% polyacrylamide gels. FIG. 2 is a schematic of an exemplary pT7BPI construct so produced.

The expression host, *E. coli* strain JM109(DE3), was transformed using 1 $\mu$l of the mini-plasmid preparation and the Kanahan transformation protocol. JM109(DE3) contains a chromosomal copy of the gene for T7 RNA polymerase which can be induced with IPTG. The transformed bacteria were plated on LB plates containing carbamicillin and incubated overnight at 37° C. Results are shown in FIGS. 1A–1E.

Since the full-length and proline-212 truncated forms of BPI protein containing the signal peptide do not give colonies while those forms that do not contain the signal peptide do give colonies, the BPI protein was expressed in an active form and is processed correctly, sending the protein to the periplasmic space of the bacteria (the location in bacteria that proteins possessing a signal peptide are sent to) where the bactericidal activity kills the cell. This also implies that both the full-length form and the proline-212 truncated form are active and capable of bactericidal activity.

Whether the forms of BPI protein which do not contain the signal peptide are active or are prevented from exhibiting their bactericidal activity by being sequestered in the cell (either by the formation of inclusion bodies or by the inability to gain access to the plasma membrane due to the absence of the signal peptide or both) is not known.

rBPI was purified as follows

Conditioned media containing recombinant BPI (rBPI) was purified to 95% homogeneity in a single step over CM-Sepharose. The CM-Sepharose column (Pharmacia, Piscataway, N.J.) was first washed in five column volumes of 0.5 M NaOH followed by rinsing with pyrogen free buffers or water until no pyrogen could be detected by the Limulus Amebocyte Lysate Assay (Whittaker, Walkersville, Md.). The column was then equilibrated in 50 mM Tris pH 7.4. The conditioned media was then loaded and the bound protein was eluted in 50 mM Tris 1M NaCl pH 7.4. rBPI was concentrated and further purified by loading onto a second CM-Sepharose column equilibrated in 50 mM Tris pH 7.4 and eluted using a gradient of 0.01–1.0M NaCl. BPI elutes at approximately 0.75M NaCl. rBPI thus purified appeared as a single band on SDS-polyacrylamide gel electrophoresis and as a single peak on reverse phase HPLC.

EXAMPLE 3

Inhibition of endotoxin-induced TNF Production by BPI

Human peripheral blood mononuclear cells were isolated on Ficoll-Paque (Pharmacia) gradients, washed 2× in pyrogen free HBSS (Hazelton), and resuspended at $5\times10^6$/ml in RPMI (Gibco) media without serum. Two hundred μl of this cell suspension was incubated in each well of flat-bottom 96 well tissue culture dishes (Costar) for 2 hours at 37° C. Nonadherent cells were removed by washing 2× with RPMI+10% autologous heat inactivated serum. Adherent mononuclear cells were stimulated with *E. coli* 0111:B4 endotoxin which had been preincubated for 30 minutes at 37° C. with buffer, BPI protein or polymyxin B (Gibco; 7900 U/ml). Supernatants were harvested four hours after endotoxin mixtures were added. Secretion of TNFα was quantitated by ELISA (Endogen) (results at Table 3). Several lots of natural and recombinant BPI from CHO cells were tested.

TABLE 3

| BPI Protein | ENDOTOXIN DOSE: 10 ng/ml endotoxin | | | | 1 ng/ml endotoxin | | | | 0 ng/ml endotoxin |
|---|---|---|---|---|---|---|---|---|---|
| (nM): | 0 | 7.3 | 1.4 | 0.3 | 0 | 7.3 | 1.4 | 0.3 | 0 |
| Control | 626 | — | — | — | 334 | — | — | — | 113 |
| 78038n | — | 129 | 159 | 203 | — | 153 | 187 | 165 | — |
| 148104n | — | 98 | 104 | 162 | — | 98 | 119 | 162 | — |
| 148113n | — | 92 | 114 | 151 | — | 71 | 129 | 155 | — |
| 148159r | — | 82 | 158 | 155 | — | 87 | 136 | 147 | — |
| 148165r | — | 124 | 128 | 138 | — | 116 | 129 | 146 | — |
| 148179r | — | 85 | 139 | 134 | — | 93 | 131 | 166 | — |

n = natural
r = recombinant

EXAMPLE 4

The pathophysiologic consequences of gram negative sepsis are primarily mediated by the release of bacterial endotoxin (LPS). Since BPI Protein has endotoxin neutralizing activity in vitro, the effects of BPI Protein in vivo were studied in experimental models of endotoxic shock.

Specifically, in one experiment one group of 8 rats (Sprague Dawley rats) was given a single, bolus injection of 1 mg BPI Protein per kg body weight four hours before a single intravenous bolus of 0.5 mg/kg body weight 0111:B4 endotoxin obtained from Sigma. In the same experiment, a second group of 8 rats was given a single bolus injection of 1 mg BPI Protein per kg body weight simultaneously with a single intravenous bolus of 0.5 mg/kg body weight 0111:B4 LIPS. Further, a third group of 5 rats was given a single bolus injection of 1 mg BPI Protein per kg body weight four hours after a single intravenous bolus of 0.5 mg/kg body weight 011:B4 LPS. Finally, a fourth group of 10 rats was treated with endotoxin alone. The rats were observed for 48 hours and the survival recorded for each group. The results of this experiment are shown in Table 4. Rats to which endotoxin alone was administered exhibited a mortality rate of 80%. Rats which received both BPI Protein and endotoxin showed a significantly reduced mortality rate. The results set forth in Table 4 establish BPI Protein is useful in vivo both to prevent and to treat disorders associated with the presence of endotoxin. High dose BPI Protein toxicity studies revealed no evidence of toxicity when the animals were sacrificed at 7 days. We conclude BPI is a non-toxic naturally occurring protein which binds LPS, inhibits release of TNF and reduces mortality in both endotoxin and GNB experimental sepsis models (FIG. 17). We believe BPI Protein offers a novel immunotherapeutic approach to the management of septic shock.

TABLE 4

INVESTIGATION OF THE POTENTIAL PROTECTIVE EFFICACY OF BPI IN THE RAT ENDOTOXIN CHALLENGE MODEL

| Endotoxin Dose Survival | BPI Protein Dose | BPI Protein Administration Regimen | % |
|---|---|---|---|
| 0.5 mg/kg (2/10) | — | — | 0 |
| 0.5 mg/kg (6/8) | 1 mg/kg | 4 hr pre-injection | 5 |
| 0.5 mg/kg (4/8) | 1 mg/kg | simultaneous | 8 |
| 0.5 mg/kg (4/5) | 1 mg/kg | 4 hr post-injection | 8 |

Additionally, in a second experiment with Bactericidal/Permeability Increasing Protein (BPI) neutropenic rats were challenged with Pseudomonas (PA1244) during a period of neutropenia. One group of rats was treated with 10 mg BPI/kg of body weight by intravenous administration at the onset of fever at day 5 and observed through day 11. A second group of rats was treated at the onset of fever with buffer containing saline at day 5 and observed until day 11. After day 8, the rat group treated with buffer was found dead; however, the rat group treated with BPI Protein exhibited 60% survival. The rats were observed for 11 days and the survival recorded for each group. At day 11, no additional deaths occurred for the rat group treated with BPI. The results of this experiment are shown in FIG. 15. FIG. 15 is a line graph showing that (1) during and after day 8 the rat group treated with buffer experienced a 100% mortality rate and (2) during and after day 7 the rat group treated with BPI Protein exhibited about a 40% mortality rate. The rats which received BPI Protein showed a significantly reduced mortality rate.

Human BPI Protein at does up to 10 mg/kg intravenously (IV) produced no acute hexatologic, biochemical, or pathologic abnormalities in outbred CD-1 mice or Sprague-Dawley rats (Table 5). Infusion of 1 mg/kg of *E. coli* 0111:B4 endotoxin IV in 6 CD-1 mice resulted in a 100% (6/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 100% (4/4), 100% (4/4) and 100 (5/5), respectively.

Infusion of 10 mg/kg of *E. coli* 0111:B4 endotoxin IV in 6 CD-1 mice resulted in a 17% (1/6) survival rate in control CD-1 mice. The survival rate in BPI Protein treated mice infused with 1 mg/kg of

TABLE 5

BPI PROTEIN PROTECTS AGAINST LETHALITY FROM ENDOTOXIC SHOCK (CD-1MICE)

| Endotoxin Challenge (*E. Coli* 0111:B4) | % SURVIVAL (NO. SURVIVORS/TOTAL NO. ANIMALS TESTED) | | | |
|---|---|---|---|---|
| | Control (Saline) | BPI 1 mg/kg IV | BPI 2 mg/kg IV | BPI 1 0 mg/kg IV |
| * 1 mg/kg IV | 100 (6/6) | 100 (4/4) | 100 (4/4) | 100 (5/5) |
| * 10 mg/kg IV | 17 (1/6) | 50 (2/4) | 100 (4/4) | 100 (5/5) |
| * 50 mg/kg IV | 0 (0/6) | 25 (1/4) | 25 (1/4) | 100 (5/5) |

TABLE 5-continued

BPI PROTEIN PROTECTS AGAINST LETHALITY FROM ENDOTOXIC SHOCK (CD-1MICE)

| Endotoxin Challenge (*E. Coli* 0111:B4) | % SURVIVAL (NO. SURVIVORS/TOTAL NO. ANIMALS TESTED) | | | |
|---|---|---|---|---|
| | Control (Saline) | BPI 1 mg/kg IV | BPI 2 mg/kg IV | BPI 1 0 mg/kg IV |
| * 100 mg/kg IV | 0 (0/6) | 0 (0/4) | 0 (0/4) | 80 (4/5) |
| * 200 mg/kg IV | 0 (0/6) | 0 (0/4) | 0 (0/4) | 20 (1/5) |

*E. coli* 0111:B4 endotoxin IV at 1 mg/kg BPI Protein IV, 2 mg/kg BPI Protein IV, and 10 mg/kg BPI Protein IV was 50% (2/4), 100% (4/4) and 100 (5/5), respectively.

Infusion of 50 mg/kg of *E. coli* 0111:B4 endotoxin IV in 6 CD-1 mice resulted in a 0% (0/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 25% (1/4), 25% (1/4) and 25 (5/5), respectively.

Infusion of 100 mg/kg of *E. coli* 0111:B4 endotoxin IV in 6 CD-1 mice resulted in a 0% (0/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 0% (0/4), 0% (0/4) and 80% (4/5), respectively.

Infusion of 200 mg/kg of *E. coli* 0111:B4 endotoxin IV in 6 CD-1 mice resulted in a 0% (0/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 0% (0/4), 0% (0/4) and 20% (1/5), respectively.

In conclusion, Table 5 demonstrates that BPI Protein is non-toxic in experimental animals and provides significant protection from lethality following endotoxin challenge (FIG. 16). This naturally occurring, neutrophil derived, antimicrobial protein provides a new therapeutic strategy in the treatment of septic shock.

Human BPI Protein at does up to 10 mg/kg intravenously (IV) produced no acute hexatologic, biochemical, or pathologic abnormalities in outbred CD-1 mice (Table 6). Using CD-1 mice, the in vivo efficacy of BPI Protein against endotoxin was tested by infusing 50 mg/kg of *E. coli* 0111:B4 endotoxin IV in 10 mice resulted in a 100% (0/10) survival rate in control CD-1 mice. The survival rate for BPI Protein treated mice infused with 50 mg/kg of *E. coli* 0111:B4 endotoxin IV at 10 mg/kg BPI Protein IV was 0% (0/10). The p value is $p<0.001$. Further, 5 mice were infused with 50 mg/kg of 055 IV (as control) which resulted in a 0% (0/5) survival rate. The survival rate for BPI Protein treated mice infused with of 50 mg/kg 055 IV at 10 mg/kg BPI Protein IV was 100% (5/5). The p value is $p<0.01$. Additionally, 5 mice were infused with 25 mg/kg of Rc rough mutant (core glycolipid) IV (as control) which resulted in a 0% (0/5) survival rate. The survival rate for BPI Protein treated mice infused with 25 mg/kg of Rc rough mutant (core glycolipid)IV at 10 mg/kg BPI Protein IV was 100% (5/5). The p value is $p<0.01$. Also, 4 mice were infused with 25 mg/kg of Lipid A IV (as control) which resulted in a 0% (0/4) survival rate. The survival rate for BPI Protein treated mice infused with 25 mg/kg of Lipid A IV at 10 mg/kg BPI Protein IV was 100% (5/5). The p value is $p<0.05$.

BPI is a non-toxic naturally occurring protein with endotoxin neutralizing activity which reduces mortality in both endotoxic and bacteremic models of sepsis syndrome and may be a useful immunotherapeutic approach to the management of the septic shock.

TABLE 6

EFFECT OF BPI PROTEIN ON LETHALITY OF VARIOUS ENDOTOXIN PHENOTYPES

| | % Survival (No. Surviving/No. Animals Tested) | | |
|---|---|---|---|
| endotoxin Phenotype | BPI 10 mg/kg | Control | p Value |
| * 0111:B4 50 mg/kg | 100 (10/10) | 0 (1/10) | p < 0.001 |
| * 055 50 mg/kg | 100 (5/5) | 0 (0/5) | P = 0.01 |
| * Rc Rough mutant (core glycolipid) 25 mg/kg | 100 (5/5) | 0 (0/5) | p = 0.01 |
| * Lipid A 25 mg/kg | 100 (5/5) | 0 (0/4) | p < 0.05 |

In order to generate a non-glycosylated form of the BPI molecule, the (CHO) cell line which normally expresses glycosylated recombinant BPI Protein (clone 3Al), was grown to confluence in roller bottles (Costar, Cambridge, Mass.) in REM 020 (Hazelton, Inc. Denver, Pa.) containing 7.5% dialyzed bovine serum (Gibco)+2 μg/ml tunicamycin (Boehringer Mannheim, Indianapolis, Ind.). After 24 hours, the medium was discarded, and replaced with fresh complete medium containing 2 μ/ml tunicamycin. Conditioned medium was collected and replaced every 24 hours for three days. Non-glycosylated recombinant BPI Protein was purified as described in Example 3 above for recombinant BPI Protein and further separated from residual glycosylated recombinant BPI Protein by Superose 12 (Pharmacia) size exclusion chromatography in 20 mM glycine+100 mM NaCl at PH 2. Fractions containing nonglycosylated BPI Protein (identified by polyacrylamide gel electrophoresis) were pooled.

Glycosylated or nonglycosylated recombinant BPI Protein was injected into mice at 10 mg/kg. Blood was collected at the indicated times through the retroorbital plexus. Blood samples were then allowed to clot, the fibrin clot was removed by centrifugation, and the recombinant BPI Protein levels were determined by ELISA assay (results are shown in FIG. 18).

ELISA ASSAY
EQUIPMENT
Immulon-2 96 well plates (Dynatech)
12-channel 50–200 μL pipettor
P20, P200, P1000 pipettors
Reagent reservoirs (Costar)
Racked 1 ml tubes (BioRad)
polypropylene 15 ml conical tubes
REAGENTS
SOLUTIONS
25 Mm Borate pH 9.5
Blocking solution = 5% BSA (Sigma Fraction V, Low -continued Endotoxin) in PBS
Wash/Sample Buffer: 50 mM Tris pH 7.4
500 mM NaCl
1 mg/ml BSA
0.05% Tween 20
1 μ/ml Polymyxin B Sulfate
(Gibco/BRL, 7900 U/mg)
BPI standard (aliquots stored @ - 70° C.)
NOTE: BPI standards and samples should be diluted in polypropylene
Standard and sample diluent = appropriate solution for unknowns
(e.g. if testing tissue culture supernatants, use REM + 7.5% dFBS)
Substrate Buffer: (makes 500 ml)
24.5 mg $MgCl_2$
48 ml ethanolamine
bring up to - 400 ml with Lab V $H_2O$
Adjust to pH 9.8
Bring up to 500 ml with Lab V $H_2O$
PNPP substrate tablets (5 mg/tablet: Sigma)
ANTIBODIES
Capture (1st) Antibody (100 μl/well)
A. INVN 1-2 (rabbit polyclonal anti-human BPI Protein) IgG 1 μg/ml, or,
B. NM-1 (rabbit anti N-terminal 20 amino acid BPI peptide) 3 μg/ml.
Reporter (2nd) Antibody
A. INVN 1-2-Biotin (Use @ 1:1000)
B. PIG8 (murine monoclonal anti-BPI which blocks BPI binding to bacteria
Third (developing) reagent
A. Streptavidin/Alkaline Phosphatase (BioRad) (use @ 1:2000)
B. Goat anti-mouse Ig/Alkaline Phosphatase conjugate (BioRad) (use @ 1:2000)
PROCEDURE
1. COATING PLATES
Note: Coat plates up to 1 month in advance.
Store plates at 4° C. until needed.
Dilute capture antibody as directed in 25 mM Na Borate pH 9.5 (10 ml/plate).
Add 100 μl to cach well of 96 well plate (Immulan-2).
Incubate overnight at 37° C.
Refrigerate until used.
2. BLOCKING
Flick coating antibody out of plates.
Add 200 μl 5% BSA in PBS to each well.
Incubate 2–4 hours 37° C. or overnight at 4° C..
Wash 4X with wash solution and blot an paper towels.
3. BPI STANDARDS AND UNKNOWNS
STANDARDS
Thaw new standard aliquot (0.5 ml @ 1 mg/ml) every 2 months.
1. Make 1 ml stack solution of purified or BPI at 100 ng/ml
2. Make 500 μl of each of the following standard concentrations as follows:

| μl 100 ng/ml BPI | μ diluent | final [BPI] ng/ml |
|---|---|---|
| 150 | 350 | 30 |
| 100 | 400 | 20 |
| 75 | 425 | 15 |
| 50 | 450 | 10 |
| 40 | 460 | 8 |
| 25 | 475 | 5 |
| 10 | 490 | 2 |
| 0 | 50 | 0 |

Add 100 μl standard (unknown) / well and incubate at RT for 2–4 hours, or overnight at 4° C..
wash 4X
2nd ANTIBODY
After final wash, blot plate vigorously, and add 100 μl of INVN1-2-Biotinylated @ 1:1000 (=10 μl in 10 ml of wash/sample buffer) to each well.
Incubate 37° C. 1 hour -continued

| |
|---|
| Wash 4X |
| 3rd ANTIBODY |
| After final wash, blot plate vigorously, and add 100 μl developing reagent to each well. |
| Incubate 37° C. 30 minutes |
| Wash 4X |
| SUBSTRATE |
| NOTE: Add substrate tablets to substrate buffer just before adding to plate. |
| After final wash, blot plate vigorously, and add 100 μl substrate solution (2X 5 mg PNPP substrate tablet/10 ml substrate buffer) |
| Read plate at 405 nm. Keep plate in the dark between readings. |

Varying concentrations of BPI protein were detected using the sandwich ELISA assay performed according to the protocol above. The ELISA was performed in the presence and absence of 1 μg/ml polymyxin B sulfate and the presence or absence of 1 μg/ml *E. coli* 0111 B4 endotoxin using PBS plus 1% BSA as the diluent. The results are shown in FIG. 4. Thus, where the sample is a biological fluid sample, BPI can be detected using an ELISA assay as described above. The amount of BPI in a biological sample can be determined by comparing the ELISA results of the biological sample of to the standard curve for BPI shown in FIG. 3.

EXAMPLE 5

Biologically Active Variants of BPI: Several classes of variants of BPI were constructed to alter some of the different properties of the native molecule (SEQ ID NOS: 13 and 14). In the first type of construct, variants were designed to extend the molecular half-life in serum. In one of such constructs, the single glycosylation site at Ser351 was altered by making a single base pair change at position 1175 (FIG. 12) so that it encodes Ala and would not support N-glycosylation (i.e. Ser351->AlaBPI(nonglycosylated) (SEQ ID NO: 18) at Table 7). This change was made by amplifying this particular segment of the molecule by PCR using amplifiers containing the desired sequence, and then replacing the native segment with the corrected segment by virtue of convenient restriction sites (the SphI site at base 1202 in this case). Such a molecule was expected to possess similar properties as BPI but may be cleared less rapidly by the liver since it would lack the mannose residues recognized by hepatic clearance receptors. Other constructs were designed to take advantage of the apparent high stability of LBP, a homolog of BPI. For instance, the amino-terminal 25 kDa segment (presumably the endotoxin-binding domain) of LBP was combined with the carboxy-terminal 30 kDa portion of BPI to create a chimeric molecule with the greater serum half-life of LBP but the functionality of BPI (i.e. LBP25K/BPI30K chimeric (SEQ ID NO:17) at Table 7).

A third type of construct utilized the extraordinary serum stability of immunoglobin to extend the stability of BPI. The amino-terminal 25 kDa (LPS-binding) portion of BPI was linked to cDNA encoding the constant domain of $IgG_1$. The resultant chimeric molecule could be expected to bind endotoxin and inactivate it like the anti-endotoxin antibodies currently under development.

A second class of molecules were designed to enhance the therapeutic index of BPI Protein. For example, the amino terminal domain of BPI Protein contains a very high proportion of positively-charged residues (approximately 14%). In several of the variants, one or more of the amino terminal cationic residues were changed to neutral or negatively charged residues by the methods described below. Such redesigned molecules may prove less disruptive to biological membranes and therefore be less cationic. Also, the LBP/BPI Protein chimeric molecule described below (i.e. LBP25K/BP130K chimeric at Table 7) may also be less toxic due to the reduced cationicity of the LBP amino terminal domain relative to BPI.

A third class of variants were intended to increase the affinity, specificity, and/or valency of endotoxin binding to BPI. For example, recombinant BPI Protein containing single base pair changes within the 25 kDA portion were produced and tested for their ability to bind endotoxin in vitro. Changing certain key amino acids, particularly cationic residues, may enhance the affinity of BPI Protein for its ligand, i.e. endotoxin. Also, the LBP/BPI Protein chimeric molecule designated LBP25K/BPI30K chimeric may have the affinity of LPB for endotoxin, while possessing the functionality of BPI. Other constructs added a second endotoxin-binding domain to BPI, under the expectation that it may bind twice the amount of endotoxin per BPI Protein.

A fourth class of mutants were designed to modify the binding affinity of BPI and/or BPI/endotoxin complexes for the receptors with which it normally interacts to downregulate macrophage activation. Examples of this include BPI Protein with single amino acid changes within the 30 kDa portion of BPI, created by in vitro mutagenesis as described below. One such mutant designated BPI25K/DP/BPI30K (SEQ ID NO: 19) (Table 7) created a variant from which the intact 25 kDA domain could be liberated by treatment with formic acid.

Methods used to create the biologically active variants of BPI were standard as practiced in the art. Relevant portions of key molecules were recombined to form chimeric molecules through commonly used methods. For example, the amino-terminal 25 kDa portion of LBP was linked to the carboxy-terminal portion of BPI Protein by virtue of an engineered ClaI site within the coding sequence (SEQ ID NO: 27), as shown in FIG. 26. Oligonucleotide amplimers (SEQ ID NOS: 20–25 and 27) containing cloning sites as well as a segment of DNA sufficient to hybridize to stretches at both ends of the target cDNA (25 bases) were synthesized chemically by standard methods. These primers were then used to amplify the desired gene segments by Polymerase Chain Reaction. The resulting new gene segments were digested with the corresponding restriction enzyme under standard conditions, and were isolated by gel electrophoresis. Alternately, similar gene segments were produced by digestion of the cDNA itself with appropriate restriction enzymes, and filling in missing gene segments with chemically synthesized oligonucleotides. These segments of coding sequence were ligated together and cloned into appropriate expression vectors which would allow recombinant production of the encoded sequence. Relevant expression systems for such chimeric molecules include but are not limited to mammalian cells such as CHO, fungi such as yeast, insect viruses such as baculavirus, and bacteria such as *E. coli*. For each of these systems, a useful expression vector would include antibiotic resistance gene such as ampicillin which would allow selection of recombinant clones; a second antibiotic resistance gene to allow selection on the host cells, such as neomycin; a bacterial replication origin to allow propagation in bacteria; a high level promoter upstream of the gene insertion site, such as the MMTV, SV40, or metallothionine promoter for CHO cells, the trp, lac, tac or T7 promoter for bacterial hosts, or the alpha factor, gal, or PGDH promoters in yeast; transcription enhancers for the mammalian hosts, such as the RSV enhancer; and a polyadenylation site, AATAAA, if one does not exist within the cDNA sequence. Once homogeneous cultures of recombinant cells were obtained through standard culture methods, large quantities of recombinant chimeric molecules were recovered and analyzed from the conditioned medium through standard chromatographic methods.

As examples, three of the constructs described above were constructed in vector pMamNeo, a commercially available expression vector (Clontech, Mountain View, Calif.), and used to transform mammalian cell host DUXB11. After transformation using lipofectin, a commercially available reagent (BRL/Gibco Gaithersberg, Md.), the cells were cultured in standard tissue culture medium to allow recovery and phenotypic expression of neomycin resistance. After 24 hours of recovery, the selective agent G418 was added to the medium to select for cells expressing the introduced genes. After three weeks of culture in selective media, drug resistant cell pools were obtained and grown to confluent densities. At this time, media was removed and assayed for the presence of immunoreactivity to anti-BPI Protein by ELISA, and for binding to endotoxin prebound to multiwell plates. In some cases, 160 nM dexamethasone was added to the medium to enhance expression because the vector also contained a glucocorticoid binding site in the promoter region. The levels of BPI Protein produced were monitored in each supernatant sample taken, and representative date is shown below:

TABLE 7

| Culture | Description | ELISA ng/ml | Endotoxin Binding ng/ml |
|---|---|---|---|
| A | LBP25K/BP130K chimeric | 4.3 | 7.8 |
| B | Ser182->AlaBPI (nonglycosylated) | 8.3 | 10.8 |
| C | BP125K/DP/BPI30K | 5.8 | 5.2 |
| D | BPI | 3.9 | 3.7 |

Therefore, these three biologically active variants of BPI were shown to be produced in CHO hosts, were immunologically crossreactive with anti-BPI Antibody, and able to bind endotoxin at levels similar to BPI. The same vector was transfected into alternate cell host lines to see of improved levels could be achieved. Constructs from which large quantities of recombinant protein was desired were also recloned into an amplifyable vector such as pSE, containing the gene encoding dihydrofolate reductase.

What is claimed is:

1. A recombinant analog of bactericidal/permeability-increasing protein (BPI) wherein the analog has the amino acid sequence as shown in FIG. 24 (SEQ ID NO: 18) or FIG. 25 (SEQ ID NO: 19).

2. A recombinant analog according to claim 1, wherein the analog (1) specifically binds to endotoxin, (2) competes with BPI protein for binding to endotoxin, and (3) inhibits endotoxin-induced lethality.

* * * * *

SEQUENCE LISTING

```
(1) GENERAL INFORMATION:

   (iii) NUMBER OF SEQUENCES: 27


(2) INFORMATION FOR SEQ ID NO:1:

     (i) SEQUENCE CHARACTERISTICS:
          (A) LENGTH: 8 amino acids
          (B) TYPE: amino acid
          (C) STRANDEDNESS: Not Relevant
          (D) TOPOLOGY: linear

    (ii) MOLECULE TYPE: protein

    (xi) SEQUENCE DESCRIPTION: SEQ ID NO:1:

Ile Asn Tyr Gly Leu Val Ala Pro
1               5


(2) INFORMATION FOR SEQ ID NO:2:

     (i) SEQUENCE CHARACTERISTICS:
          (A) LENGTH: 36 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:2:

TAGAACTATG GTCTGGTGGC ACCTTGAGGA TCCGCG                              36


(2) INFORMATION FOR SEQ ID NO:3:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear
```

-continued (ii) MOLECULE TYPE: DNA (xi) SEQUENCE DESCRIPTION: SEQ ID NO:3:

CGCGGATCCT CAAGGTGCCA CCAGACCATA 30

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

CGCGGATCCT CAAGGTGCCA CCAGACCATA 30

(2) INFORMATION FOR SEQ ID NO:5:

(i) SEQUENCE CHARACTERISTICS:
(A) LENGTH: 8 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:5:

Pro Thr Gly Leu Thr Phe Tyr Pro
1 5

(2) INFORMATION FOR SEQ ID NO:6:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

CCCACCGGCC TTACCTTCTA CCCTTGAGGA TCCGCG 36

(2) INFORMATION FOR SEQ ID NO:7:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

CGCGGATCCT CAAGGGTAGA AGGTAAGGCC 30

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA -continued (xi) SEQUENCE DESCRIPTION: SEQ ID NO:8:

CGCGGATCCT CAAGGGTAGA AGGTAAGGCC 30

(2) INFORMATION FOR SEQ ID NO:9:

(i) SEQUENCE CHARACTERISTICS:
(A) LENGTH: 6 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:9:

Met Arg Glu Asn Met Arg
1 5

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

CCCAAGCTTG CCACCATGAG AGAGAACATG GCC 33

(2) INFORMATION FOR SEQ ID NO:11:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

CCCAAGCTTG CCACCATGAG AGAGAACATG GCC 33

(2) INFORMATION FOR SEQ ID NO:12:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

AAAAAAACCC GAGATCCGCG GATCCTTTCC T 31

(2) INFORMATION FOR SEQ ID NO:13:

(i) SEQUENCE CHARACTERISTICS:
(A) LENGTH: 487 amino acids
(B) TYPE: amino acid
(D) TOPOLOGY: linear (ii) MOLECULE TYPE: protein (xi) SEQUENCE DESCRIPTION: SEQ ID NO:13:

Met Arg Glu Asn Met Ala Arg Gly Pro Cys Asn Ala Pro Arg Trp Val
1 5 10 15

-continued

```
Ser Leu Met Val Leu Val Ala Ile Gly Thr Ala Val Thr Ala Ala Val
            20                  25                  30

Asn Pro Gly Val Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Lys Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
    290                 295                 300

Gly Val Leu Lys Met Thr Leu Arg Asp Asp Met Ile Pro Lys Glu Ser
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
        355                 360                 365

Ala Val Asp Val Gln Ala Phe Ala Val Leu Pro Asn Ser Ser Leu Ala
    370                 375                 380

Ser Leu Phe Leu Ile Gly Met His Thr Thr Gly Ser Met Glu Val Ser
385                 390                 395                 400

Ala Glu Ser Asn Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430
```

-continued

```
Gln Asp Ile Met Asn Tyr Ile Val Pro Ile Leu Val Leu Pro Arg Val
        435                 440                 445

Asn Glu Lys Leu Gln Lys Gly Phe Pro Leu Pro Thr Pro Ala Arg Val
    450                 455                 460

Gln Leu Tyr Asn Val Val Leu Gln Pro His Gln Asn Phe Leu Leu Phe
465                 470                 475                 480

Gly Ala Asp Val Val Tyr Lys
                485
```

(2) INFORMATION FOR SEQ ID NO:14:

(i) SEQUENCE CHARACTERISTICS:
(A) LENGTH: 1813 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

```
CAGGCCTTGA GGTTTTGGCA GCTCTGGAGG ATGAGAGAGA ACATGGCCAG GGGCCCTTGC     60

AACGCGCCGA GATGGGTGTC CCTGATGGTG CTCGTCGCCA TAGGCACCGC CGTGACAGCG    120

GCCGTCAACC CTGGCGTCGT GGTCAGGATC TCCCAGAAGG GCCTGGACTA CGCCAGCCAG    180

CAGGGGACGG CCGCTCTGCA GAAGGAGCTG AAGAGGATCA AGATTCCTGA CTACTCAGAC    240

AGCTTTAAGA TCAAGCATCT TGGGAAGGGG CATTATAGCT TCTACAGCAT GGACATCCGT    300

GAATTCCAGC TTCCCAGTTC CCAGATAAGC ATGGTGCCCA ATGTGGGCCT TAAGTTCTCC    360

ATCAGCAACG CCAATATCAA GATCAGCGGG AAATGGAAGG CACAAAAGAG ATTCTTAAAA    420

ATGAGCGGCA ATTTTGACCT GAGCATAGAA GGCATGTCCA TTTCGGCTGA TCTGAAGCTG    480

GGCAGTAACC CCACGTCAGG CAAGCCCACC ATCACCTGCT CCAGCTGCAG CAGCCACATC    540

AACAGTGTCC ACGTGCACAT CTCAAAGAGC AAAGTCGGGT GGCTGATCCA ACTCTTCCAC    600

AAAAAAATTG AGTCTGCGCT TCGAAACAAG ATGAACAGCC AGGTCTGCGA GAAAGTGACC    660

AATTCTGTAT CCTCCAAGCT GCAACCTTAT TTCCAGACTC TGCCAGTAAT GACCAAAATA    720

GATTCTGTGG CTGGAATCAA CTATGGTCTG GTGGCACCTC CAGCAACCAC GGCTGAGACC    780

CTGGATGTAC AGATGAAGGG GGAGTTTTAC AGTGAGAACC ACCACAATCC ACCTCCCTTT    840

GCTCCACCAG TGATGGAGTT TCCCGCTGCC CATGACCGCA TGGTATACCT GGGCCTCTCA    900

GACTACTTCT TCAACACAGC CGGGCTTGTA TACCAAGAGG CTGGGGTCTT GAAGATGACC    960

CTTAGAGATG ACATGATTCC AAAGGAGTCC AAATTTCGAC TGACAACCAA GTTCTTTGGA   1020

ACCTTCCTAC CTGAGGTGGC CAAGAAGTTT CCCAACATGA AGATACAGAT CCATGTCTCA   1080

GCCTCCACCC CGCCACACCT GTCTGTGCAG CCCACCGGCC TTACCTTCTA CCCTGCCGTG   1140

GATGTCCAGG CCTTTGCCGT CCTCCCCAAC TCCTCCCTGG CTTCCCTCTT CCTGATTGGC   1200

ATGCACACAA CTGGTTCCAT GGAGGTCAGC GCCGAGTCCA ACAGGCTTGT TGGAGAGCTC   1260

AAGCTGGATA GGCTGCTCCT GGAACTGAAG CACTCAAATA TTGGCCCCTT CCCGGTTGAA   1320

TTGCTGCAGG ATATCATGAA CTACATTGTA CCCATTCTTG TGCTGCCCAG GGTTAACGAG   1380

AAACTACAGA AAGGCTTCCC TCTCCCGACG CCGGCCAGAG TCCAGCTCTA CAACGTAGTG   1440

CTTCAGCCTC ACCAGAACTT CCTGCTGTTC GGTGCAGACG TTGTCTATAA ATGAAGGCAC   1500

CAGGGGTGCC GGGGGCTGTC AGCCGCACCT GTTCCTGATG GGCTGTGGGG CACCGGCTGC   1560

CTTTCCCCAG GGAATCCTCT CCAGATCTTA ACCAAGAGCC CCTTGCAAAC TTCTTCGACT   1620
```

-continued

```
CAGATTCAGA AATGATCTAA ACACGAGGAA ACATTATTCA TTGGAAAAGT GCATGGTGTG   1680

TATTTTAGGG ATTATGAGCT TCTTTCAAGG GCTAAGGCTG CAGAGATATT TCCTCCAGGA   1740

ATCGTGTTTC AATTGTAACC AAGAAATTTC CATTTGTGCT TCATGAAAAA AACTTCTGG    1800

TTTTTTTCAT GTG                                                      1813
```

(2) INFORMATION FOR SEQ ID NO:15:

(i) SEQUENCE CHARACTERISTICS:
(A) LENGTH: 368 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:15:

```
Met Arg Glu Asn Met Ala Arg Gly Pro Cys Asn Ala Pro Arg Trp Val
1               5                   10                  15

Ser Leu Met Val Leu Val Ala Ile Gly Thr Ala Val Thr Ala Ala Val
            20                  25                  30

Asn Pro Gly Val Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Lys Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
    290                 295                 300

Gly Val Leu Lys Met Thr Leu Arg Asp Asp Met Ile Pro Lys Glu Ser
```

-continued

```
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
        355                 360                 365
```

(2) INFORMATION FOR SEQ ID NO:16:

(i) SEQUENCE CHARACTERISTICS:
(A) LENGTH: 243 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:16:

```
Met Arg Glu Asn Met Ala Arg Gly Pro Cys Asn Ala Pro Arg Trp Val
1               5                   10                  15

Ser Leu Met Val Leu Val Ala Ile Gly Thr Ala Val Thr Ala Ala Val
            20                  25                  30

Asn Pro Gly Val Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Lys Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro
```

(2) INFORMATION FOR SEQ ID NO:17:

(i) SEQUENCE CHARACTERISTICS:
(A) LENGTH: 454 amino acids
(B) TYPE: amino acid
(C) STRANDEDNESS: Not Relevant
(D) TOPOLOGY: linear -continued (ii) MOLECULE TYPE: protein (xi) SEQUENCE DESCRIPTION: SEQ ID NO:17:

```
Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
        35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
            100                 105                 110

Ile Ser Val Asn Leu Leu Leu Gly Ser Glu Ser Ser Gly Arg Pro Thr
        115                 120                 125

Gly Tyr Cys Leu Ser Cys Ser Ser Asp Ile Ala Asp Val Glu Val Asp
    130                 135                 140

Met Ser Gly Asp Ser Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile Asp Ser Val Ala Gly Ile Asn Tyr Gly Leu Val
        195                 200                 205

Ala Pro Pro Ala Thr Thr Ala Glu Thr Leu Asp Val Gln Met Lys Gly
    210                 215                 220

Glu Phe Tyr Ser Glu Asn His His Asn Pro Pro Pro Phe Ala Pro Pro
225                 230                 235                 240

Val Met Glu Phe Pro Ala Ala His Asp Arg Met Val Tyr Leu Gly Leu
                245                 250                 255

Ser Asp Tyr Phe Phe Asn Thr Ala Gly Leu Val Tyr Gln Glu Ala Gly
            260                 265                 270

Val Leu Lys Met Thr Leu Arg Asp Asp Met Ile Pro Lys Glu Ser Lys
        275                 280                 285

Phe Arg Leu Thr Thr Lys Phe Phe Gly Thr Phe Leu Pro Glu Val Ala
    290                 295                 300

Lys Lys Phe Pro Asn Met Lys Ile Gln Ile His Val Ser Ala Ser Thr
305                 310                 315                 320

Pro Pro His Leu Ser Val Gln Pro Thr Gly Leu Thr Phe Tyr Pro Ala
                325                 330                 335

Val Asp Val Gln Ala Phe Ala Val Leu Pro Asn Ser Ser Leu Ala Ser
            340                 345                 350

Leu Phe Leu Ile Gly Met His Thr Thr Gly Ser Met Glu Val Ser Ala
        355                 360                 365

Glu Ser Asn Arg Leu Val Gly Glu Leu Lys Leu Asp Arg Leu Leu Leu
    370                 375                 380

lu Leu Lys His Ser Asn Ile Gly Pro Phe Pro Val Glu Leu Leu Gln
385                 390                 395                 400
```

-continued

Asp Ile Met Asn Tyr Ile Val Pro Ile Leu Val Leu Pro Arg Val Asn
405 410 415

Glu Lys Leu Gln Lys Gly Phe Pro Leu Pro Thr Pro Ala Arg Val Gln
420 425 430

Leu Tyr Asn Val Val Leu Gln Pro His Gln Asn Phe Leu Leu Phe Gly
435 440 445

Ala Asp Val Val Tyr Lys
450

(2) INFORMATION FOR SEQ ID NO:18:

(i) SEQUENCE CHARACTERISTICS:
(A) LENGTH: 456 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:18:

Val Asn Pro Gly Val Val Val Arg Ile Ser Gln Lys Gly Leu Asp Tyr
1 5 10 15

Ala Ser Gln Gln Gly Thr Ala Ala Leu Gln Lys Glu Leu Lys Arg Ile
20 25 30

Lys Ile Pro Asp Tyr Ser Asp Ser Phe Lys Ile Lys His Leu Gly Lys
35 40 45

Gly His Tyr Ser Phe Tyr Ser Met Asp Ile Arg Glu Phe Gln Leu Pro
50 55 60

Ser Ser Gln Ile Ser Met Val Pro Asn Val Gly Leu Lys Phe Ser Ile
65 70 75 80

Ser Asn Ala Asn Ile Lys Ile Ser Gly Lys Trp Lys Ala Gln Lys Arg
85 90 95

Phe Leu Lys Met Ser Gly Asn Phe Asp Leu Ser Ile Glu Gly Met Ser
100 105 110

Ile Ser Ala Asp Leu Lys Leu Gly Ser Asn Pro Thr Ser Gly Lys Pro
115 120 125

Thr Ile Thr Cys Ser Ser Cys Ser Ser His Ile Asn Ser Val His Val
130 135 140

His Ile Ser Lys Ser Lys Val Gly Trp Leu Ile Gln Leu Phe His Lys
145 150 155 160

Lys Ile Glu Ser Ala Leu Arg Asn Lys Met Asn Ser Gln Val Cys Glu
165 170 175

Lys Val Thr Asn Ser Val Ser Ser Lys Leu Gln Pro Tyr Phe Gln Thr
180 185 190

Leu Pro Val Met Thr Lys Ile Asp Ser Val Ala Gly Ile Asn Tyr Gly
195 200 205

Leu Val Ala Pro Pro Ala Thr Thr Ala Glu Thr Leu Asp Val Gln Met
210 215 220

Lys Gly Glu Phe Tyr Ser Glu Asn His His Asn Pro Pro Pro Phe Ala
225 230 235 240

Pro Pro Val Met Glu Phe Pro Ala Ala His Asp Arg Met Val Tyr Leu
245 250 255

Gly Leu Ser Asp Tyr Phe Phe Asn Thr Ala Gly Leu Val Tyr Gln Glu
260 265 270

Ala Gly Val Leu Lys Met Thr Leu Arg Asp Asp Met Ile Pro Lys Glu
275 280 285

-continued

Ser Lys Phe Arg Leu Thr Thr Lys Phe Phe Gly Thr Phe Leu Pro Glu
    290                 295                 300

Val Ala Lys Lys Phe Pro Asn Met Lys Ile Gln Ile His Val Ser Ala
305                 310                 315                 320

Ser Thr Pro Pro His Leu Ser Val Gln Pro Thr Gly Leu Thr Phe Tyr
                325                 330                 335

Pro Ala Val Asp Val Gln Ala Phe Ala Val Leu Pro Asn Ser Ala Leu
            340                 345                 350

Ala Ser Leu Phe Leu Ile Gly Met His Thr Thr Gly Ser Met Glu Val
        355                 360                 365

Ser Ala Glu Ser Asn Arg Leu Val Gly Glu Leu Lys Leu Asp Arg Leu
    370                 375                 380

Leu Leu Glu Leu Lys His Ser Asn Ile Gly Pro Phe Pro Val Glu Leu
385                 390                 395                 400

Leu Gln Asp Ile Met Asn Tyr Ile Val Pro Ile Leu Val Leu Pro Arg
                405                 410                 415

Val Asn Glu Lys Leu Gln Lys Gly Phe Pro Leu Pro Thr Pro Ala Arg
            420                 425                 430

Val Gln Leu Tyr Asn Val Val Leu Gln Pro His Gln Asn Phe Leu Leu
        435                 440                 445

Phe Gly Ala Asp Val Val Tyr Lys
    450                 455

(2) INFORMATION FOR SEQ ID NO:19:

(i) SEQUENCE CHARACTERISTICS:
(A) LENGTH: 456 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:19:

Val Asn Pro Gly Val Val Val Arg Ile Ser Gln Lys Gly Leu Asp Tyr
1               5                   10                  15

Ala Ser Gln Gln Gly Thr Ala Ala Leu Gln Lys Glu Leu Lys Arg Ile
            20                  25                  30

Lys Ile Pro Asp Tyr Ser Asp Ser Phe Lys Ile Lys His Leu Gly Lys
        35                  40                  45

Gly His Tyr Ser Phe Tyr Ser Met Asp Ile Arg Glu Phe Gln Leu Pro
    50                  55                  60

Ser Ser Gln Ile Ser Met Val Pro Asn Val Gly Leu Lys Phe Ser Ile
65                  70                  75                  80

Ser Asn Ala Asn Ile Lys Ile Ser Gly Lys Trp Lys Ala Gln Lys Arg
                85                  90                  95

Phe Leu Lys Met Ser Gly Asn Phe Asp Leu Ser Ile Glu Gly Met Ser
            100                 105                 110

Ile Ser Ala Asp Leu Lys Leu Gly Ser Asn Pro Thr Ser Gly Lys Pro
        115                 120                 125

Thr Ile Thr Cys Ser Ser Cys Ser Ser His Ile Asn Ser Val His Val
    130                 135                 140

His Ile Ser Lys Ser Lys Val Gly Trp Leu Ile Gln Leu Phe His Lys
145                 150                 155                 160

Lys Ile Glu Ser Ala Leu Arg Asn Lys Met Asn Ser Gln Val Cys Glu
                165                 170                 175

-continued

```
Lys Val Thr Asn Ser Val Ser Ser Lys Leu Gln Pro Tyr Phe Gln Thr
            180                 185                 190

Leu Pro Val Met Thr Lys Ile Asp Pro Val Ala Gly Ile Asn Tyr Gly
        195                 200                 205

Leu Val Ala Pro Pro Ala Thr Thr Ala Glu Thr Leu Asp Val Gln Met
    210                 215                 220

Lys Gly Glu Phe Tyr Ser Glu Asn His His Asn Pro Pro Pro Phe Ala
225                 230                 235                 240

Pro Pro Val Met Glu Phe Pro Ala Ala His Asp Arg Met Val Tyr Leu
                245                 250                 255

Gly Leu Ser Asp Tyr Phe Phe Asn Thr Ala Gly Leu Val Tyr Gln Glu
            260                 265                 270

Ala Gly Val Leu Lys Met Thr Leu Arg Asp Asp Met Ile Pro Lys Glu
        275                 280                 285

Ser Lys Phe Arg Leu Thr Thr Lys Phe Phe Gly Thr Phe Leu Pro Glu
    290                 295                 300

Val Ala Lys Lys Phe Pro Asn Met Lys Ile Gln Ile His Val Ser Ala
305                 310                 315                 320

Ser Thr Pro Pro His Leu Ser Val Gln Pro Thr Gly Leu Thr Phe Tyr
                325                 330                 335

Pro Ala Val Asp Val Gln Ala Phe Ala Val Leu Pro Asn Ser Ser Leu
            340                 345                 350

Ala Ser Leu Phe Leu Ile Gly Met His Thr Thr Gly Ser Met Glu Val
        355                 360                 365

Ser Ala Glu Ser Asn Arg Leu Val Gly Glu Leu Lys Leu Asp Arg Leu
    370                 375                 380

Leu Leu Glu Leu Lys His Ser Asn Ile Gly Pro Phe Pro Val Glu Leu
385                 390                 395                 400

Leu Gln Asp Ile Met Asn Tyr Ile Val Pro Ile Leu Val Leu Pro Arg
                405                 410                 415

Val Asn Glu Lys Leu Gln Lys Gly Phe Pro Leu Pro Thr Pro Ala Arg
            420                 425                 430

Val Gln Leu Tyr Asn Val Val Leu Gln Pro His Gln Asn Phe Leu Leu
        435                 440                 445

Phe Gly Ala Asp Val Val Tyr Lys
    450                 455
```

(2) INFORMATION FOR SEQ ID NO:20:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

```
TATCATGCTA G                                                          11
```

(2) INFORMATION FOR SEQ ID NO:21:

(i) SEQUENCE CHARACTERISTICS:
(A) LENGTH: 21 base pairs
(B) TYPE: nucleic acid
(C) STRANDEDNESS: single
(D) TOPOLOGY: linear -continued (ii) MOLECULE TYPE: DNA (xi) SEQUENCE DESCRIPTION: SEQ ID NO:21:

CAGGCCTTGA GGTTTTGGCA G 21

(2) INFORMATION FOR SEQ ID NO:22:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:22:

CTGCCAGTAA TGACCAAAAT CGATCCTGTG GCTGGAATC 39

(2) INFORMATION FOR SEQ ID NO:23:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

GATTCTGTGG CTGGAATC 18

(2) INFORMATION FOR SEQ ID NO:24:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

GTCTGCAACA GATATTTACT TGAGCTCATG CAG 33

(2) INFORMATION FOR SEQ ID NO:25:

(i) SEQUENCE CHARACTERISTICS:
(A) LENGTH: 103 amino acids
(B) TYPE: amino acid
(D) TOPOLOGY: linear (ii) MOLECULE TYPE: protein (xi) SEQUENCE DESCRIPTION: SEQ ID NO:25:

```
Met Arg Glu Asn Met Ala Arg Gly Pro Cys Asn Ala Pro Arg Trp Val
  1               5                  10                  15

Ser Leu Met Val Leu Val Asn Lys Met Asn Ser Gln Val Cys Glu Lys
            20                  25                  30

Val Thr Asn Ser Val Ser Ser Lys Leu Gln Pro Tyr Phe Gln Thr Leu
        35                  40                  45

Pro Val Met Thr Lys Ile Asp Ser Val Ala Gly Ile Asn Tyr Gly Leu
    50                  55                  60

Val Ala Pro Pro Ala Thr Thr Ala Glu Thr Leu Asp Val Gln Met Lys
 65                  70                  75                  80

Gly Glu Phe Tyr Ser Glu Leu Gln Pro His Gln Asn Phe Leu Leu Phe
```

-continued

```
                  85                  90                  95

Gly Ala Asp Val Val Tyr Lys
            100
```

(2) INFORMATION FOR SEQ ID NO:26:

(i) SEQUENCE CHARACTERISTICS:
(A) LENGTH: 432 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:26:

```
CAGGCCTTGA GGTTTTGGCA GCTCTGGAGG ATGAGAGAGA ACATGGCCAG GGGCCCTTGC     60

AACGCGCCGA GATGGGTGTC CCTGATGGTG CTCGTCAACA AGATGAACAG CCAGGTCTGC    120

GAGAAAGTGA CCAATTCTGT ATCCTCCAAG CTGCAACCTT ATTTCCAGAC TCTGCCAGTA    180

ATGACCAAAA TAGATTCTGT GGCTGGAATC AACTATGGTC TGGTGGCACC TCCAGCAACC    240

ACGGCTGAGA CCCTGGATGT ACAGATGAAG GGGGAGTTTT ACAGTGAGCT TCAGCCTCAC    300

CAGAACTTCC TGCTGTTCGG TGCAGACGTT GTCTATAAAT GAAGGCACCA GGGGTGCCGG    360

GGGCTGTCAG CCGCACCTGT TCCTGATGGG CTGTGGGGCA CCGGCTGCCT TTCCCCAGGG    420

AATCCTCTCC AG                                                        432
```

(2) INFORMATION FOR SEQ ID NO:27:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:27:

```
CTGCCAGTAA TGACCAAAAT C                                               21
```